US008784425B2

(12) United States Patent
Ritchey et al.

(10) Patent No.: US 8,784,425 B2
(45) Date of Patent: Jul. 22, 2014

(54) SYSTEMS AND METHODS FOR IDENTIFYING LANDMARKS ON ORTHOPEDIC IMPLANTS

(75) Inventors: Nicholas S. Ritchey, Collierville, TN (US); Henry B. Faber, Memphis, TN (US); Nathaniel Kelley Grusin, Germantown, TN (US); James K. Rains, Cordova, TN (US); Gene Edward Austin, Bartlett, TN (US); Tobias Schwägli, Solothurn (CH); William M. Ricci, Richmond Heights, MO (US)

(73) Assignee: Smith & Nephew, Inc., Memphis, TN (US)

( * ) Notice: Subject to any disclaimer, the term of this patent is extended or adjusted under 35 U.S.C. 154(b) by 332 days.

(21) Appl. No.: 12/547,716

(22) Filed: Aug. 26, 2009

(65) Prior Publication Data

US 2010/0152573 A1 Jun. 17, 2010

Related U.S. Application Data

(63) Continuation-in-part of application No. 12/527,997, filed as application No. PCT/US2008/055300 on Feb. 28, 2008, now Pat. No. 8,739,801.

(60) Provisional application No. 61/173,069, filed on Apr. 27, 2009, provisional application No. 60/892,116, filed on Feb. 28, 2007, provisional application No. 60/911,907, filed on Apr. 15, 2007.

(51) Int. Cl.
*A61B 17/58* (2006.01)
*A61B 17/17* (2006.01)

(52) U.S. Cl.
CPC .................................. *A61B 17/1707* (2013.01)
USPC .............................................. 606/96; 128/899

(58) Field of Classification Search
CPC . A61B 17/1707; A61B 19/5251; A61B 5/067
USPC ......... 606/62, 67, 72, 86, 96, 97, 98; 128/899
See application file for complete search history.

(56) References Cited

U.S. PATENT DOCUMENTS

| 3,219,969 A | 11/1965 | Snavely |
| 4,353,110 A | 10/1982 | Ellis |

(Continued)

FOREIGN PATENT DOCUMENTS

| CN | 2698283 Y | 5/2005 |
| DE | 102008023760 | 12/2009 |

(Continued)

OTHER PUBLICATIONS

Ekliptik, Guiding Star, Lidis: The Best Solution for Distal Interlocking, 2008, 2 pages.

(Continued)

*Primary Examiner* — Ellen C Hammond
*Assistant Examiner* — Stuart S Bray
(74) *Attorney, Agent, or Firm* — Fish & Richardson P.C.

(57) ABSTRACT

Systems (10, 110, 1010, 1110) for identifying landmarks (31, 131, 1028, 1128) on orthopedic implants (30, 130, 1024, 1124) are disclosed. The systems (10, 110, 1010, 1110) include a field generator (16, 116, 1016, 1116) for generating a magnetic field and an orthopedic implant (30, 130, 1024, 1124) located within the magnetic field. The implant (30, 130, 1024, 1124) includes at least one landmark (31, 131, 1028, 1128), an optional removable probe (1029, 1129) and a first magnetic sensor (32, 132, 1026, 1126). The systems (10, 110, 1010, 1110) further include a landmark identifier (18, 118, 1016, 1116) with an optional second magnetic sensor (20, 120, 1020, 1120) and a processor (12, 112, 1012, 1112) for comparing sensor data from the first sensor (32, 132, 1026, 1126) and second sensor (20, 120, 1020, 1120) or data from the first sensor (32, 132, 1026,1126) and landmark identifier (18, 118, 1016, 1116) using the set distance to calculate the position of the landmark identifier (18, 118, 1016, 1116) relative to the at least one landmark (31, 131, 1028,1128). The disclosed systems (10, 110, 1010, 1110) allow for blind targeting of one or more landmarks (31, 131, 1028, 1128).

22 Claims, 24 Drawing Sheets

(56) References Cited

U.S. PATENT DOCUMENTS

| | | | |
|---|---|---|---|
| 4,532,599 A | 7/1985 | Smith | |
| 4,621,628 A | 11/1986 | Brudermann | |
| D297,047 S | 8/1988 | Hon et al. | |
| 4,794,930 A | 1/1989 | Machida et al. | |
| 4,803,976 A | 2/1989 | Frigg et al. | |
| 5,049,151 A | 9/1991 | Durham et al. | |
| 5,127,913 A * | 7/1992 | Thomas, Jr. | 606/62 |
| 5,217,009 A | 6/1993 | Kronberg | |
| 5,251,127 A | 10/1993 | Raab | |
| 5,281,224 A | 1/1994 | Faccioli et al. | |
| 5,361,766 A | 11/1994 | Nichols et al. | |
| 5,383,917 A | 1/1995 | Desai et al. | |
| 5,411,503 A | 5/1995 | Hollstien et al. | |
| 5,417,688 A | 5/1995 | Elstrom et al. | |
| 5,433,720 A | 7/1995 | Faccioli et al. | |
| 5,514,145 A | 5/1996 | Durham et al. | |
| 5,580,156 A | 12/1996 | Suzuki et al. | |
| 5,584,838 A | 12/1996 | Rona et al. | |
| 5,585,783 A | 12/1996 | Hall | |
| 5,957,836 A | 9/1999 | Johnson | |
| 5,957,934 A | 9/1999 | Rapoport | |
| 6,009,878 A | 1/2000 | Weijand et al. | |
| 6,036,696 A | 3/2000 | Lambrecht et al. | |
| 6,039,742 A | 3/2000 | Krettek et al. | |
| 6,074,394 A | 6/2000 | Krause | |
| 6,081,741 A | 6/2000 | Hollis | |
| 6,106,528 A * | 8/2000 | Durham et al. | 606/64 |
| 6,157,853 A | 12/2000 | Blume et al. | |
| 6,162,228 A | 12/2000 | Durham | |
| 6,174,335 B1 | 1/2001 | Varieur et al. | |
| 6,212,419 B1 | 4/2001 | Blume et al. | |
| 6,233,490 B1 | 5/2001 | Kasevich | |
| 6,267,770 B1 | 7/2001 | Truwit | |
| 6,304,091 B1 | 10/2001 | Shahoian et al. | |
| 6,311,082 B1 | 10/2001 | Creighton et al. | |
| 6,474,341 B1 | 11/2002 | Hunter et al. | |
| 6,503,249 B1 * | 1/2003 | Krause | 606/62 |
| 6,575,973 B1 * | 6/2003 | Shekalim | 606/62 |
| 6,636,757 B1 | 10/2003 | Jascob et al. | |
| 6,675,491 B2 | 1/2004 | Sasaki et al. | |
| 6,694,168 B2 | 2/2004 | Traxel et al. | |
| 6,718,194 B2 | 4/2004 | Kienzle | |
| 6,747,253 B1 | 6/2004 | Firth et al. | |
| 6,807,446 B2 | 10/2004 | Fenn et al. | |
| 6,890,332 B2 | 5/2005 | Truckai et al. | |
| 6,991,655 B2 | 1/2006 | Iversen | |
| 7,001,346 B2 | 2/2006 | White | |
| 7,029,478 B2 | 4/2006 | Hollstien et al. | |
| 7,060,075 B2 * | 6/2006 | Govari et al. | 606/98 |
| D528,211 S | 9/2006 | Solar et al. | |
| 7,130,676 B2 | 10/2006 | Barrick | |
| 7,152,608 B2 | 12/2006 | Hunter et al. | |
| 7,217,276 B2 | 5/2007 | Henderson et al. | |
| 7,253,611 B2 | 8/2007 | Ma | |
| 7,294,133 B2 | 11/2007 | Zink et al. | |
| 7,295,184 B2 | 11/2007 | Suprun et al. | |
| 7,358,481 B2 | 4/2008 | Yeoh et al. | |
| 7,477,926 B2 | 1/2009 | McCombs | |
| 7,532,997 B2 | 5/2009 | Li et al. | |
| 7,542,791 B2 | 6/2009 | Mire et al. | |
| 7,549,960 B2 * | 6/2009 | Govari | 600/437 |
| 7,559,931 B2 | 7/2009 | Stone | |
| 7,575,550 B1 | 8/2009 | Govari | |
| 7,634,306 B2 | 12/2009 | Sarin et al. | |
| 7,686,818 B2 * | 3/2010 | Simon et al. | 606/130 |
| 7,702,379 B2 | 4/2010 | Avinash et al. | |
| 7,727,240 B1 * | 6/2010 | Benton | 606/98 |
| 7,729,742 B2 * | 6/2010 | Govari | 600/424 |
| 7,780,681 B2 | 8/2010 | Sarin et al. | |
| 7,785,330 B2 | 8/2010 | Sherman et al. | |
| 7,835,785 B2 | 11/2010 | Scully et al. | |
| 7,840,254 B2 | 11/2010 | Glossop | |
| 7,846,162 B2 | 12/2010 | Nelson et al. | |
| 7,918,853 B2 * | 4/2011 | Watanabe et al. | 606/64 |
| 7,925,068 B2 | 4/2011 | Hoctor et al. | |
| 7,927,338 B2 | 4/2011 | Laffargue et al. | |
| 7,949,386 B2 | 5/2011 | Buly et al. | |
| 7,955,280 B2 | 6/2011 | Radinsky et al. | |
| 8,007,448 B2 | 8/2011 | Moctezuma | |
| 8,066,706 B2 * | 11/2011 | Schlienger et al. | 606/64 |
| 8,167,823 B2 | 5/2012 | Nycz et al. | |
| 8,176,922 B2 * | 5/2012 | Sherman et al. | 128/899 |
| 8,197,494 B2 | 6/2012 | Jaggi et al. | |
| 8,211,108 B2 * | 7/2012 | Matityahu | 606/64 |
| 8,241,296 B2 | 8/2012 | Wasielewski | |
| 8,301,262 B2 | 10/2012 | Mi et al. | |
| 8,337,426 B2 | 12/2012 | Nycz | |
| 8,623,023 B2 * | 1/2014 | Ritchey et al. | 606/86 R |
| 2002/0032445 A1 | 3/2002 | Fujiwara | |
| 2002/0052604 A1 * | 5/2002 | Simon et al. | 606/62 |
| 2002/0077540 A1 | 6/2002 | Kienzle | |
| 2002/0173792 A1 * | 11/2002 | Severns et al. | 606/62 |
| 2003/0105470 A1 | 6/2003 | White | |
| 2003/0120150 A1 | 6/2003 | Govari | |
| 2003/0135211 A1 * | 7/2003 | Cho | 606/62 |
| 2003/0153829 A1 | 8/2003 | Sarin et al. | |
| 2003/0164172 A1 | 9/2003 | Chumas et al. | |
| 2003/0208122 A1 | 11/2003 | Melkent et al. | |
| 2004/0011365 A1 * | 1/2004 | Govari et al. | 128/899 |
| 2004/0034355 A1 * | 2/2004 | Govari et al. | 606/72 |
| 2004/0097952 A1 | 5/2004 | Sarin et al. | |
| 2004/0147926 A1 | 7/2004 | Iversen | |
| 2004/0230199 A1 | 11/2004 | Jansen et al. | |
| 2004/0243148 A1 | 12/2004 | Wasielewski | |
| 2004/0254584 A1 | 12/2004 | Sarin et al. | |
| 2005/0027301 A1 | 2/2005 | Stihl | |
| 2005/0027304 A1 | 2/2005 | Leloup et al. | |
| 2005/0035115 A1 | 2/2005 | Anderson et al. | |
| 2005/0035116 A1 | 2/2005 | Brown et al. | |
| 2005/0043726 A1 | 2/2005 | McHale et al. | |
| 2005/0059885 A1 | 3/2005 | Melkent et al. | |
| 2005/0070916 A1 | 3/2005 | Hollstien et al. | |
| 2005/0075562 A1 * | 4/2005 | Szakelyhidi et al. | 600/424 |
| 2005/0075632 A1 | 4/2005 | Russell et al. | |
| 2005/0080335 A1 * | 4/2005 | Simon et al. | 600/424 |
| 2005/0080427 A1 * | 4/2005 | Govari et al. | 606/98 |
| 2005/0085714 A1 | 4/2005 | Foley et al. | |
| 2005/0085715 A1 | 4/2005 | Dukesherer et al. | |
| 2005/0099290 A1 | 5/2005 | Govari | |
| 2005/0124988 A1 | 6/2005 | Terrill et al. | |
| 2005/0143726 A1 | 6/2005 | Bortkiewicz | |
| 2005/0148855 A1 | 7/2005 | Kienzle | |
| 2005/0149050 A1 | 7/2005 | Stifter et al. | |
| 2005/0197569 A1 | 9/2005 | McCombs | |
| 2005/0228270 A1 | 10/2005 | Lloyd et al. | |
| 2005/0242087 A1 | 11/2005 | Anderson et al. | |
| 2005/0245821 A1 | 11/2005 | Govari et al. | |
| 2005/0261700 A1 | 11/2005 | Tuma et al. | |
| 2006/0015031 A1 | 1/2006 | Kienzle, III | |
| 2006/0029186 A1 | 2/2006 | De Villiers et al. | |
| 2006/0052782 A1 | 3/2006 | Morgan et al. | |
| 2006/0074405 A1 | 4/2006 | Malackowski et al. | |
| 2006/0084867 A1 | 4/2006 | Tremblay et al. | |
| 2006/0095047 A1 | 5/2006 | de la Barrera | |
| 2006/0106400 A1 | 5/2006 | Fernandez et al. | |
| 2006/0142656 A1 | 6/2006 | Malackowski et al. | |
| 2006/0190011 A1 | 8/2006 | Ries | |
| 2006/0264731 A1 | 11/2006 | Murphy | |
| 2006/0282168 A1 * | 12/2006 | Sherman et al. | 623/18.12 |
| 2006/0287613 A1 | 12/2006 | Amiot et al. | |
| 2006/0293593 A1 | 12/2006 | Govari et al. | |
| 2006/0293614 A1 | 12/2006 | Radinsky et al. | |
| 2007/0093709 A1 | 4/2007 | Abernathie | |
| 2007/0129629 A1 | 6/2007 | Beauregard et al. | |
| 2007/0162018 A1 | 7/2007 | Jensen et al. | |
| 2007/0167744 A1 | 7/2007 | Beauregard et al. | |
| 2007/0191827 A1 | 8/2007 | Lischinsky et al. | |
| 2007/0208251 A1 | 9/2007 | Anderson et al. | |
| 2007/0225595 A1 | 9/2007 | Malackowski et al. | |
| 2007/0249967 A1 | 10/2007 | Buly et al. | |
| 2007/0255132 A1 | 11/2007 | Shalgi et al. | |
| 2007/0276370 A1 | 11/2007 | Altarac et al. | |
| 2007/0282440 A1 * | 12/2007 | Visentin | 623/16.11 |
| 2008/0015551 A1 | 1/2008 | Feine | |

(56) References Cited

U.S. PATENT DOCUMENTS

| | | | |
|---|---|---|---|
| 2008/0021309 A1 | 1/2008 | Amiot et al. | |
| 2008/0039857 A1 | 2/2008 | Giersch et al. | |
| 2008/0051910 A1 | 2/2008 | Kammerzell et al. | |
| 2008/0071142 A1 | 3/2008 | Gattani et al. | |
| 2008/0086145 A1* | 4/2008 | Sherman et al. | 606/97 |
| 2008/0146969 A1 | 6/2008 | Kurtz | |
| 2008/0154266 A1 | 6/2008 | Protopsaltis et al. | |
| 2008/0221628 A1 | 9/2008 | Milbocker et al. | |
| 2008/0228195 A1 | 9/2008 | von Jako et al. | |
| 2008/0255560 A1 | 10/2008 | Myers et al. | |
| 2008/0269596 A1 | 10/2008 | Revie et al. | |
| 2008/0281326 A1* | 11/2008 | Watanabe et al. | 606/62 |
| 2008/0281334 A1 | 11/2008 | Zheng et al. | |
| 2009/0024023 A1 | 1/2009 | Welches et al. | |
| 2009/0054910 A1 | 2/2009 | Zheng et al. | |
| 2009/0088756 A1 | 4/2009 | Anderson | |
| 2009/0099404 A1 | 4/2009 | Kraus et al. | |
| 2009/0138019 A1 | 5/2009 | Wasielewski | |
| 2009/0165573 A1 | 7/2009 | Ledoux et al. | |
| 2009/0177080 A1* | 7/2009 | Kristan et al. | 600/424 |
| 2009/0227862 A1 | 9/2009 | Smith et al. | |
| 2009/0306665 A1 | 12/2009 | Lerner et al. | |
| 2009/0306666 A1* | 12/2009 | Czartoski et al. | 606/64 |
| 2009/0326537 A1 | 12/2009 | Anderson | |
| 2010/0041985 A1 | 2/2010 | Simon et al. | |
| 2010/0063508 A1 | 3/2010 | Borja et al. | |
| 2010/0064216 A1 | 3/2010 | Borja et al. | |
| 2010/0069911 A1 | 3/2010 | Borja et al. | |
| 2010/0076505 A1 | 3/2010 | Borja | |
| 2010/0100011 A1 | 4/2010 | Roche | |
| 2010/0137869 A1 | 6/2010 | Borja et al. | |
| 2010/0137871 A1 | 6/2010 | Borja | |
| 2010/0145337 A1* | 6/2010 | Janna et al. | 606/67 |
| 2010/0152566 A1* | 6/2010 | Rains et al. | 600/409 |
| 2010/0152573 A1* | 6/2010 | Ritchey et al. | 600/424 |
| 2010/0211177 A1 | 8/2010 | Abdou | |
| 2010/0249657 A1 | 9/2010 | Nycz et al. | |
| 2010/0261998 A1 | 10/2010 | Stiehl | |
| 2010/0274121 A1* | 10/2010 | Ritchey et al. | 600/424 |
| 2010/0274253 A1 | 10/2010 | Ure | |
| 2010/0274256 A1* | 10/2010 | Ritchey et al. | 606/96 |
| 2010/0274306 A1 | 10/2010 | Pastore et al. | |
| 2010/0289491 A1 | 11/2010 | Budker et al. | |
| 2010/0312245 A1* | 12/2010 | Tipirneni et al. | 606/62 |
| 2011/0082366 A1 | 4/2011 | Scully et al. | |
| 2011/0109311 A1 | 5/2011 | Walsh | |
| 2011/0130765 A1* | 6/2011 | Fernandez et al. | 606/97 |
| 2011/0208037 A1* | 8/2011 | Rains et al. | 600/409 |
| 2011/0257518 A1 | 10/2011 | Buly et al. | |
| 2011/0270080 A1 | 11/2011 | Crane | |
| 2011/0288600 A1* | 11/2011 | Ritchey et al. | 606/86 R |
| 2011/0295108 A1 | 12/2011 | Cox et al. | |
| 2011/0295253 A1* | 12/2011 | Bonutti et al. | 606/62 |
| 2012/0010500 A1 | 1/2012 | Couture et al. | |
| 2012/0022406 A1 | 1/2012 | Hladio et al. | |
| 2012/0035468 A1* | 2/2012 | Ritchey et al. | 600/424 |
| 2012/0091122 A1 | 4/2012 | Ahmad et al. | |
| 2012/0101361 A1* | 4/2012 | Rains et al. | 600/409 |
| 2012/0136402 A1 | 5/2012 | Burroughs | |
| 2012/0143047 A1 | 6/2012 | Kimura et al. | |
| 2012/0184844 A1 | 7/2012 | Gielen et al. | |
| 2012/0209117 A1 | 8/2012 | Mozes et al. | |
| 2012/0220107 A1 | 8/2012 | Fukuda et al. | |
| 2012/0226094 A1* | 9/2012 | Ritchey et al. | 600/12 |
| 2012/0227542 A1 | 9/2012 | Koch | |
| 2012/0232561 A1* | 9/2012 | Fernandez | 606/97 |
| 2012/0253354 A1* | 10/2012 | Arlettaz et al. | 606/98 |
| 2012/0283599 A1 | 11/2012 | Borja | |
| 2013/0131679 A1* | 5/2013 | Janna et al. | 606/62 |
| 2013/0218007 A1* | 8/2013 | Petteys et al. | 600/424 |
| 2013/0289573 A1* | 10/2013 | Heilala et al. | 606/96 |

FOREIGN PATENT DOCUMENTS

| | | |
|---|---|---|
| EP | 523905 | 5/1993 |
| EP | 628287 | 4/1995 |
| EP | 1391181 | 2/2004 |
| EP | 1570782 A2 | 9/2005 |
| EP | 1382308 | 11/2005 |
| EP | 1570781 | 9/2009 |
| EP | 2130511 | 12/2009 |
| EP | 1563810 B1 | 3/2010 |
| EP | 1743590 | 10/2010 |
| EP | 1803394 B1 | 1/2012 |
| GR | 1005791 | 1/2008 |
| WO | WO9500085 | 1/1995 |
| WO | WO9713467 | 4/1997 |
| WO | WO9832387 A1 | 7/1998 |
| WO | WO9947052 | 9/1999 |
| WO | WO0134016 | 10/2001 |
| WO | WO02062250 | 8/2002 |
| WO | WO03044556 A2 | 5/2003 |
| WO | WO03073951 A1 | 9/2003 |
| WO | WO03041611 A3 | 12/2003 |
| WO | WO03105659 | 12/2003 |
| WO | WO2004030556 A2 | 4/2004 |
| WO | WO2004001569 B1 | 7/2004 |
| WO | WO2004069063 | 8/2004 |
| WO | WO2004091419 A8 | 11/2004 |
| WO | WO2004112610 | 12/2004 |
| WO | WO2005023110 A1 | 3/2005 |
| WO | WO2005087125 A2 | 9/2005 |
| WO | WO2005120203 A2 | 12/2005 |
| WO | WO2006060632 A1 | 6/2006 |
| WO | WO2007025191 | 3/2007 |
| WO | WO2007009088 A3 | 5/2007 |
| WO | WO2007061890 | 5/2007 |
| WO | WO2007061890 A2 | 5/2007 |
| WO | WO2006094119 A3 | 11/2007 |
| WO | WO2007133168 | 11/2007 |
| WO | WO2008105874 | 9/2008 |
| WO | WO2008106593 | 9/2008 |
| WO | WO2009046547 A1 | 4/2009 |
| WO | WO2009108214 | 9/2009 |
| WO | WO2009131999 | 10/2009 |
| WO | WO2010011978 A1 | 1/2010 |
| WO | WO2010028046 | 3/2010 |
| WO | WO2010099247 A2 | 9/2010 |
| WO | WO2010111272 A1 | 9/2010 |
| WO | WO2010129141 | 11/2010 |
| WO | WO2010129308 A2 | 11/2010 |
| WO | WO2011060536 A1 | 5/2011 |
| WO | WO2011124661 A1 | 10/2011 |
| WO | WO2012080840 A1 | 6/2012 |
| WO | WO2013049534 A1 | 4/2013 |

OTHER PUBLICATIONS

International Search Report for International Application No. PCT/US2008/055300, mailed Sep. 17, 2008, 3 pages.
International Preliminary Report on Patentability and Written Opinion for International Application No. PCT/US2008/055300, mailed Sep. 1, 2009, 6 pages.
International Preliminary Report on Patentability and Written Opinion for International Application No. PCT/US2007/063001, mailed Sep. 1, 2009, 5 pages.
International Search Report for International Application No. PCT/US2007/063001, mailed Nov. 30, 2007, 3 pages.
Rains, et al., U.S. Appl. No. 12/919,255, filed Aug. 25, 2010.
International Search Report for International Application No. PCT/US2008/074520, mailed Jan. 23, 2009, 2 pages.
Ekliptik, "Guiding Star", reprinted from http://ekliptik.si/content/view/37/42, on Jul. 1, 2010, 2 pages.
Ritchey, et al., U.S. Appl. No. 29/376,026, filed Sep. 30, 2010.
International Search Report and Written Opinion for International Application No. PCT/US2010/032634, mailed Jan. 26, 2011, 10 pages.
International Search Report and Written Opinion for PCT/US2010/030784, mailed Oct. 29, 2010, 11 pages.

(56) References Cited

OTHER PUBLICATIONS

European Search Report for European Application No. 07830964.7, mailed Jun. 18, 2010, 4 pages.
Office Action for Chinese Application No. 200880006490.9, mailed Mar. 31, 2011, 13 pages.
International Search Report and Written Opinion for International Application No. PCT/US2010/051678, mailed Apr. 14, 2011, 8 pages.
Office Action for European Application 08872996.7-1269, Jul. 21, 2011, 5 pages.
"Innomed Hip Instruments—hohmann retractors," reprinted from http://www.innomed.net/hip_rets_hohmanns.htm on Jan. 6, 2011, 8 pages.
Office Action for U.S. Appl. No. 12/528,253, mailed Mar. 21, 2012, 9 pages.
Office Action for U.S. Appl. No. 12/758,747, mailed Apr. 10, 2012, 11 pages.
Ex Parte Quayle Action in U.S. Appl. No. 29/376,026, mailed Apr. 30, 2012, 10 pages.
Office Action for U.S. Appl. No. 12/919,255, mailed May 25, 2012.
International Search Report and Written Opinion for International Application No. PCT/US2013/027042, mailed Jun. 12, 2013.
Office Action for U.S. Appl. No. 13/123,792, mailed Jul. 2, 2013.
Communication Pursuant to Article 94(3) EPC for European Application No. 07757660.1, mailed Jun. 5, 2013.
Decision of Rejection for Japanese Application No. 2009-551851, mailed Jun. 11, 2013.
Communication Pursuant to Article 94(3) EPC for European Application No. 08730964.7, mailed Jun. 6, 2013.
Office Action for U.S. Appl. No. 13/030,801, mailed Mar. 13, 2013.
Office Action for U.S. Appl. No. 13/323,010, mailed Jun. 4, 2013.
Office Action for U.S. Appl. No. 12/527,997, mailed May 21, 2013.
International Search Report and Written Opinion for International Application No. PCT/US2012/041613, mailed Feb. 15, 2013.
Notice of Reasons for Rejection for Japanese Application No. 2012-508518 mailed Dec. 10, 2013.
Office Action in Russian Application No. 2011146914, mailed Dec. 16, 2013.
Office Action for U.S. Appl. No. 13/323,010, mailed Aug. 14, 2012.
Office Action for U.S. Appl. No. 12/528,253, mailed Aug. 16, 2012.
Office Action for U.S. Appl. No. 13/123,792, mailed Sep. 14, 2012.
First Office Action for Chinese Application No. 200880128908.3 mailed Apr. 24, 2012.
Association of Surgical Technologists, "AST Recommended Standards of Practice for Surgical Drapes," effective Apr. 13, 2008.
Ashar, Tom, "Ultrasound Guidance for Placement of Central Venous Catheters," Israeli Journal of Emergency Medicine, vol. 7, No. 2, Jun. 2007.
Buckner, C., et al., "Real-Time Sonography wth Electromagnetic Tracking Navigation for Biopsy of a Hepatic Neoplasm Seen on on Arterial Phase Computed Tomography," J Ultrasound Med 2011, 30:253-256.
"GE Heathcare: Ultrasound Imaging Accessories, vol. 6," CIVco Medical Solutions, Multi-Modality Imaging, 2011.
"Guiding Star with the LIDIS module," Ekliptik, 2007.
ekliptik, LIDIS module, brochure, 2010.
Brochure for GE Healthcare Drapes and Sterile Covers, accessed on Jun. 21, 2012, at http://www.gehealthcare.com/usen/xr/surgery/docs/SurgeryDrapes&Film.pdf.
ekliptik, "User Manual: Guiding Star/LIDIS," Jun. 16, 2010, reprinted from http://www.ekliptik.si/html/downloads/documents/manuals/LIDIS_user_manual.pdf.
Medtronic, "Orthopaedic Navigation Soluations," 2005, reprinted from http://behzadisportsdoc.com/wordpress/wp-content/uploads/2011/05/medtronic_orthonavsolution.pdf.
GE Healthcare, "Interventional X-ray, OEC C-arm," 2012.
International Search Report and Written Opinion for International Application PCT/US2012/022481, mailed Jul. 31, 2012.
Office Action for U.S. Appl. No. 12/527,997, mailed Oct. 29, 2012.
Second Office Action for Chinese Application No. 200880006490.9 mailed Apr. 26, 2012.
Office Action for Australian Patent Application No. 2008221332, dated Jun. 15, 2012.
Office Action for U.S. Appl. No. 12/758,747, mailed Nov. 15, 2012.
Office Action for U.S. Appl. No. 12/919,255, mailed Jan. 8, 2013.
Office Action for U.S. Appl. No. 12/768,689, mailed Nov. 14, 2012.
Office Action for U.S. Appl. No. 12/768,689, mailed Jun. 5, 2012.
Notice of Reasons for Rejection for Japanese Application No. 2010-548660 mailed Jan. 15, 2013.

\* cited by examiner

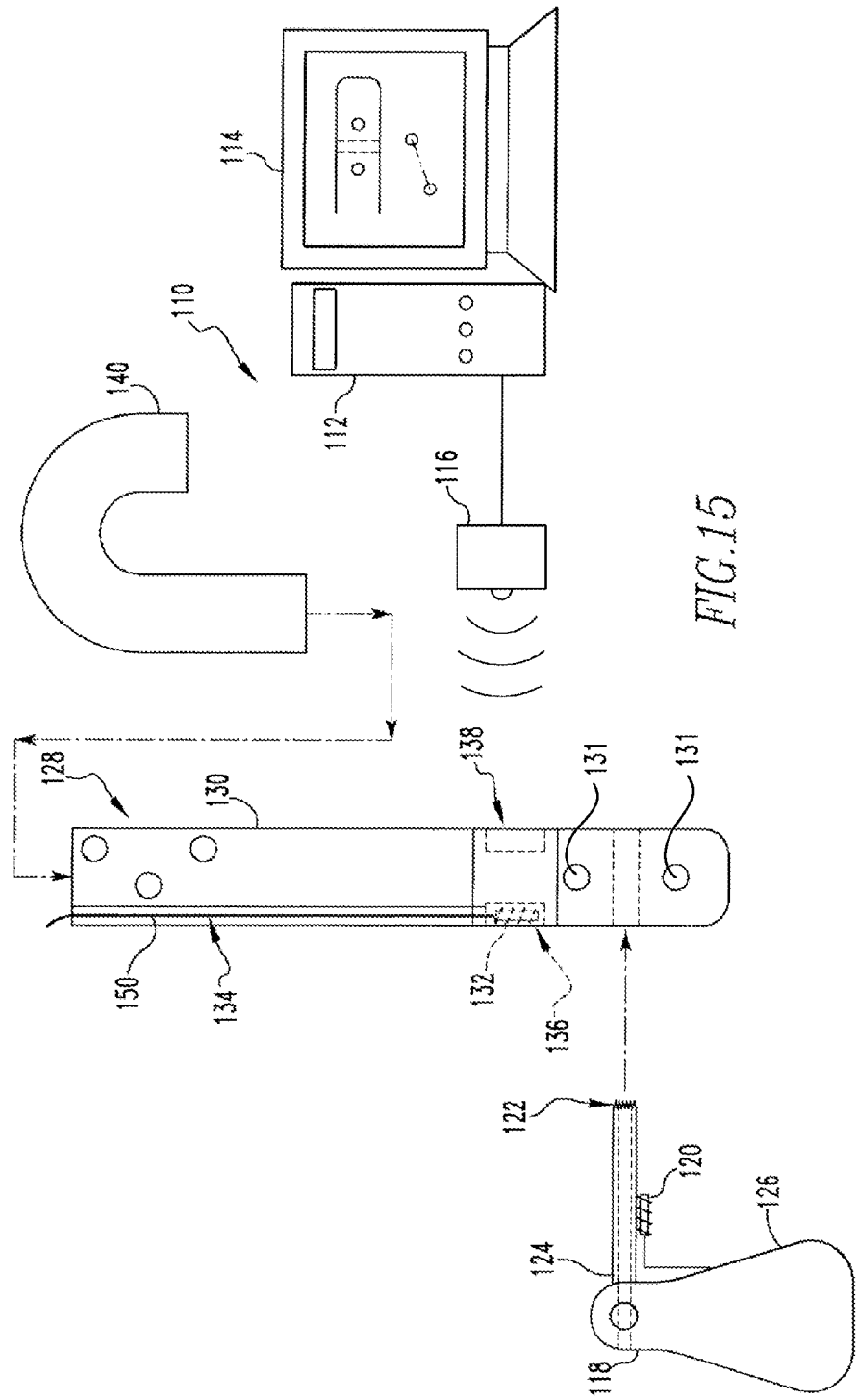

SYSTEMS AND METHODS FOR IDENTIFYING LANDMARKS ON ORTHOPEDIC IMPLANTS

CROSS REFERENCES TO RELATED APPLICATIONS

This application is a continuation-in-part of U.S. patent application Ser. No. 12/527,997, filed Aug. 20, 2009, which claims the benefit of International Patent Application No. PCT/US2008/055300, filed Feb. 29, 2008, which claims the benefit of U.S. Provisional Application Ser. No. 60/892,116, filed on Feb. 28, 2007 and U.S. Provisional Application Ser. No. 60/911,907, filed on Apr. 15, 2007. This application also claims the benefit of U.S. Provisional Application Ser. No. 61/173,069, filed on Apr. 27, 2009. The disclosures of U.S. patent application Ser. No. 12/527,997, International Application No. PCT/US2008/74520 and U.S. Provisional Application Ser. No. 61/173,069 are incorporated herein by reference in their entireties.

BACKGROUND

1. Technical Field

This disclosure relates generally to orthopedic implants and, more specifically, to identification of landmarks disposed on orthopedic implants.

2. Description of the Related Art

The development of the interlocking femoral nail has significantly widened the scope for intramedullary (IM) fixation of long bone fractures. Locking an IM nail makes the construct more stable longitudinally and stops rotation of the nail within the bone. A typical IM nail fixation surgery involves a combination of jigs, x-ray imaging, and manual "eye-balling" to locate and drill the distal screw holes.

In this surgical procedure, an IM nail is hammered into the canal of a fractured long bone in order to fixate the fractured ends together. Typically, the proximal locking is performed first and is usually carried out with a jig. Nail deformation during intramedullary insertion, however, may make a jig inaccurate for the distal screws. The primary difficulty lies in the positioning of the distal locking screws and alignment of the drill for the drilling of the distal screw holes because it is the most time consuming and challenging step of the overall implantation procedure. Consequently, the two main reasons for failure in distal locking are incorrect entry point on the bone and wrong orientation of the drill. If either of these two factors is wrong, then the drill will not go through the nail hole.

An inaccurate entry point also compounds the problem as the rounded end of the drill bit often slips, and it is then difficult to place another drill hole next to the earlier one. Inaccurate distal locking may lead to premature failure with breakage of the nail through the nail hole, breakage of the screw, or the breaking of the drill bit within the bone.

Manual techniques are the most common and accepted techniques for sighting the distal screw holes and predominate the orthopedic industry. The majority of distal targeting techniques employ a bushing (cylindrical sleeve) that guides the drill. The mechanism of aligning the guide bushing and keeping it in place differs. There are cases where the surgeons use a half sleeve (bushing cut in half longitudinally) or a full sleeve to help steady the drill bit during drilling. In either situation, the surgeon will incise the patient and insert the drill through the incision. The manual techniques are based primarily on the surgeon's manual skill and make use of radiographic x-ray imaging and mechanical jigs.

Another method for achieving this on long nails is by using a technique called "perfect circles" with the aid of a C-arm. This is where one orients the patient and the C-arm such that when viewing the implant fluoroscopically the hole with which the screw is to pass appears to be in the shape of a circle. If the C-arm is not perpendicular to the hole then it would appear oblong or even absent.

Therefore, a need exists in the art for a system and method for more accurately targeting a "landmark," target or readily identifiable feature disposed on a medical implant for more accurate placement of the medical implant and/or for interlocking, coupling or connecting one medical implant with another medical implant. Further, there remains a need in the art for accurately positioning the distal locking screws and aligning the drill for the drilling of the distal screw holes of interlocking IM nails.

SUMMARY OF THE DISCLOSURE

Various systems for identifying landmarks are disclosed. One disclosed system may comprise a field generator for generating a magnetic field; an orthopedic implant located within the magnetic field, the orthopedic implant having at least one landmark; a removable probe with a first magnetic sensor spaced apart from the at least one landmark; a landmark identifier having a second magnetic sensor; and a processor for comparing sensor data from the first and second sensor and using the set distance to calculate the position of the landmark identifier relative to the at least one landmark.

Another disclosed system for identifying a landmark may comprise: a field generator for generating a magnetic field; an orthopedic implant located within the magnetic field, the orthopedic implant having at least one landmark and a longitudinal groove with a proximal end portion and a distal end portion; a first magnetic sensor mounted to the orthopedic implant at the distal end portion of the longitudinal groove and spaced apart from the at least one landmark a set distance; a landmark identifier having a second magnetic sensor; and a processor for comparing sensor data from the first and second sensor and using the set distance to calculate the position of the landmark identifier relative to the at least one landmark.

In a refinement, the landmark may be any readily identifiable feature or element. For example, the landmark may be selected from the group consisting of a structure, a void, a boss, a channel, a detent, a flange, a groove, a member, a partition, a step, an aperture, a bore, a cavity, a dimple, a duct, a gap, a notch, an orifice, a passage, a slit, a hole, or a slot.

In a refinement, the orthopedic implant may be an intramedullary nail.

In a refinement, the orthopedic implant may have an outer surface, an inner surface forming a cannulation, and a wall therebetween, and the first magnetic sensor may be mounted within the wall.

In a refinement, the orthopedic implant may further include a pocket and the first sensor is located within a received within the pocket.

In a refinement, the orthopedic implant may further include a cover.

In a refinement, the orthopedic implant may further include a second opening adapted to receive a cover.

In a refinement, the orthopedic implant may further include a circumferential pocket.

In a refinement, the system may include a lead coupled to the first magnetic sensor.

In a refinement, the system may include an insertion handle removably coupled to the orthopedic implant.

In a refinement, the insertion handle may include a sensor.

In a refinement, the system may include a monitor electrically coupled to the processor.

In a refinement, the system may include a removable lead coupled to the first sensor.

In a refinement, the longitudinal groove may be disposed along an outer surface of the implant.

In a refinement, the orthopedic implant may also include a cannulation, and the longitudinal groove is generally adjacent the cannulation.

In a refinement, the landmark identifier may include a drill sleeve.

In a refinement, the landmark identifier may also include a serrated tip.

In a refinement, the landmark identifier may also include a tube.

In a refinement, the landmark identifier may also include a marking sensor.

In a refinement, the landmark identifier may also include a handle.

In a refinement, the field generator may be incorporated into the landmark identifier.

In a refinement, the processor may provide feedback information to a user.

Another disclosed system for identifying a landmark may comprise: a field generator for generating a magnetic field; an orthopedic implant located within the magnetic field, the orthopedic implant having at least one landmark; a magnet mounted to the orthopedic implant and spaced apart from the at least one landmark a set distance; a landmark identifier having a magnetic sensor; and a processor for comparing sensor data from the magnetic sensor and using the set distance to calculate the position of the landmark identifier relative to the at least one landmark.

A method for identifying a landmark is also disclosed that may comprise: providing an orthopedic implant assembly having an orthopedic implant with a longitudinal groove and a removable lead having a magnetic sensor attached thereto situated within the longitudinal groove, the orthopedic implant having a proximal end portion, a distal end portion, and at least one landmark on the distal end portion; implanting the orthopedic implant assembly in a patient; first installing transfixion elements in the proximal end portion; identifying the at least one landmark using a landmark identifier; installing a transfixion element in the at least one landmark in the distal end portion after first installing transfixion elements in the proximal end portion; and removing the removable lead.

A graphical user interface is also disclosed that may comprise: a first portion indicating drill depth relative to an implant; and a second portion indicating landmark identifier position relative to a landmark located on the implant.

The disclosed systems, methods and interface have several advantages over prior devices and techniques. First, the disclosed systems operate independently of fluoroscopy and eliminate the necessity of X-ray devices for targeting of transfixion elements, thereby reducing the exposure of users and patients to radiation. Second, the disclosed systems allow a user to lock the driving-end before locking the non-driving end. In other words, the disclosed systems do not require use of an implant cannulation and allows for proximal locking prior to distal locking, in some embodiments.

Further features, aspects, and advantages of the disclosed systems, methods and interfaces, as well as the structure and operation of various refinements thereof, are described in detail below with reference to the accompanying drawings.

BRIEF DESCRIPTION OF THE DRAWINGS

For a more complete understanding of the disclosed methods and apparatuses, reference should be made to the exemplary embodiments illustrated in greater detail in the accompanying drawings, wherein:

FIG. 15 illustrates another disclosed system for identifying landmarks;

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Figure 1:
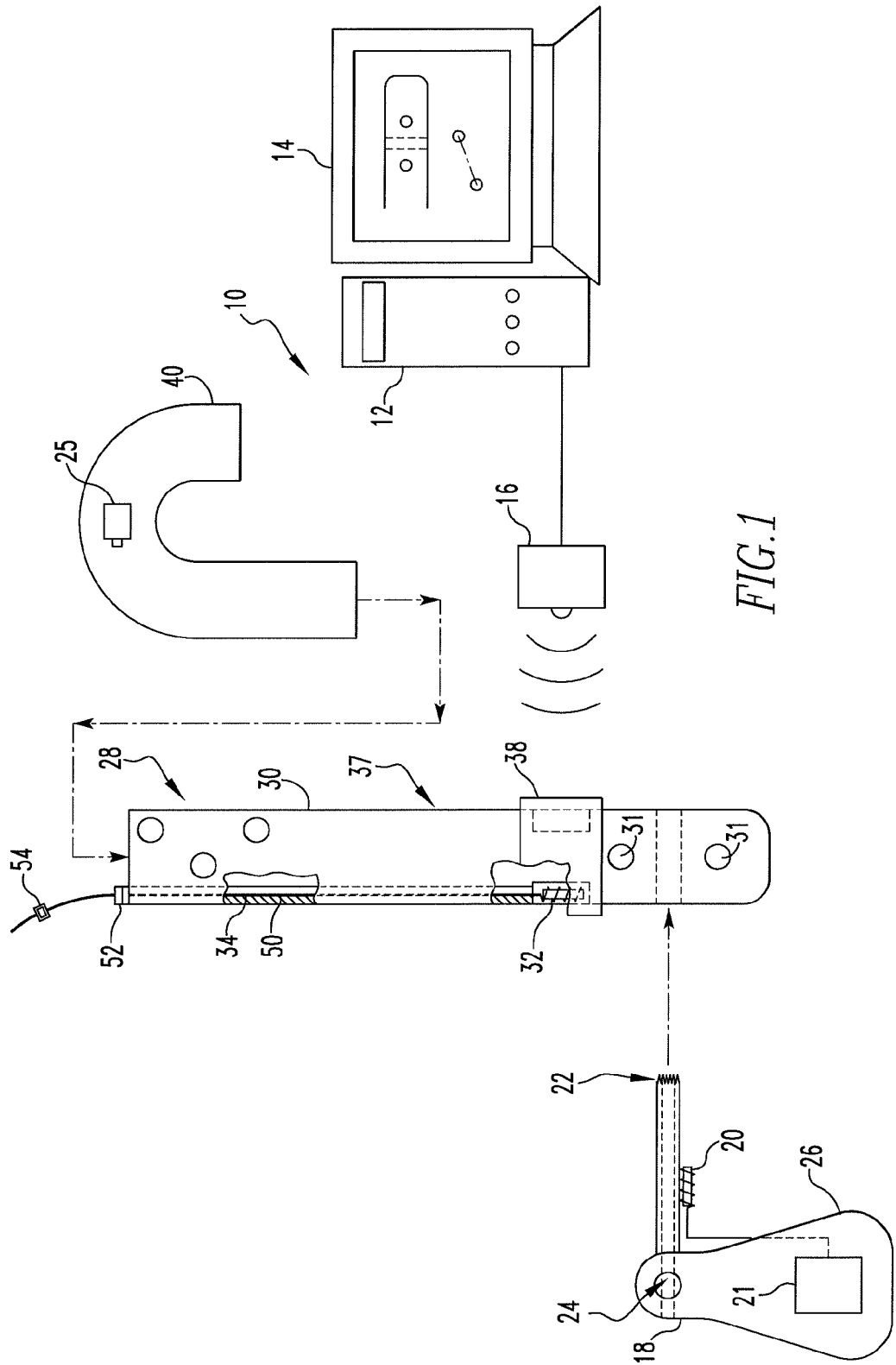
FIG. 1 illustrates a disclosed system for identifying landmarks.

Referring to the accompanying drawings in which like reference numbers indicate like elements, FIG. 1 illustrates one disclosed system 10 for identifying landmarks. The system 10 may include a processor 12, a magnetic field generator 16, a landmark identifier 18, and an orthopedic implant assembly 28. In some embodiments, the system 10 may also include a monitor 14 electrically coupled to the processor 12 and an insertion handle 40 removably attached to the orthopedic implant assembly 28. The processor 12 is depicted as a desktop computer in FIG. 1 but other types of computing devices may equally be used. As examples, the processor 12 may be a desktop computer, a laptop computer, a personal data assistant (PDA), a mobile handheld device, or a dedicated device. In the depicted embodiment, the magnetic field generator is a device available from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other generators may be used. As examples, the field generator 16 may provide a pulsed direct current electromagnetic field or an alternating current electromagnetic field. In some embodiments, the system 10 may also include a control unit (not shown) coupled to the magnetic field generator 16. The control unit controls the field generator, receives signals from small mobile inductive sensors, and communicates with the processor 12, either by wire or wirelessly. In some embodiments, the control unit may be incorporated into the processor 12 either through hardware or software.

The system 10 is a magnetic position tracking system. For illustrative purposes, the system 10 may include a magnetic field generator 16 comprised of suitably arranged electromagnetic inductive coils that serve as the spatial magnetic reference frame (i.e., X, Y, Z). The system 10 may also include small mobile inductive sensors, which are attached to the object being tracked. It should be understood that other variants could be easily accommodated. The position and angular orientation of the small mobile inductive sensors are determined from its magnetic coupling to the source field produced by magnetic field generator 16.

It is noted that the magnetic field generator 16 may generate a sequence, or set, of for example six, different spatial magnetic field shapes, or distributions, each of which is sensed by the small mobile inductive sensors. Each sequence enables a sequence of signals to be produced by the small mobile inductive sensors. Processing of the sequence of signals enables determination of position and/or orientation of the small mobile inductive sensors, and hence the position of the object to which the small mobile inductive sensor is mounted relative the magnetic coordinate reference frame which is in fixed relationship to the magnetic field generator 16. The processor 12 or the control unit uses the reference coordinate system and the sensed data to create a transformation matrix comprising position and orientation information.

The landmark identifier 18 is used to target a landmark, such as a landmark disposed on the orthopedic implant assembly 28. The landmark identifier 18 may include one or more small mobile inductive sensors. In the depicted embodiment, the landmark identifier 18 has a second sensor 20. The landmark identifier 18 may be any number of devices. As examples, the landmark identifier may be a drill guide, a drill sleeve, a drill, a drill nose, a drill barrel, a drill chuck, or a fixation element. In the embodiment depicted in FIG. 1, the landmark identifier 18 is a drill sleeve. In some embodiments, the landmark identifier may include one or more of a serrated tip 22, a tube 24, and a handle 26. The tube 24 also may be referred to as a bushing, cylinder, guide, or drilling/screw placement guide. In the depicted embodiment, the second sensor 20 is oriented relative to an axis of the tube 24, which may receive a drill. This offset of the sensor 20 from the tube 24 allows the position and orientation of the tube to be located in space in six dimensions (three translational and three angular) relative to the magnetic field generator 16 or another sensor in the system. In some embodiments, the processor 12 may need to be calibrated to adjust for the offset distance of the second sensor 20. In some embodiments, the landmark identifier 18 and the field generator 16 may be combined into a single component. For example, the field generator 16 may be incorporated within the handle 26.

The orthopedic implant assembly 28 may include an implant 30 and one or more small mobile inductive sensors. In the depicted embodiment, the orthopedic implant assembly 28 has a first sensor 32. In the embodiment depicted in FIG. 1, the implant 30 is in the form of intramedullary nail but other types of implants may be used. As examples, the implant may be an intramedullary nail, a bone plate, a hip prosthetic, or a knee prosthetic. The first sensor 32 is oriented and in a predetermined position relative to one or more landmarks on the implant 30. As examples, the landmark may any readily identifiable structure such as a void, a boss, a channel, a detent, a flange, a groove, a member, a partition, a step, an aperture, a bore, a cavity, a dimple, a duct, a gap, a notch, an orifice, a passage, a slit, a hole, or a slot. In the embodiment depicted in FIG. 1, the landmarks are transfixion holes 31. The offset of the first sensor 32 from the landmark allows the position of the landmark to be located in space in six dimensions (three translational and three angular) relative to the magnetic field generator 16 or another sensor in the system, such as the second sensor. In some embodiments, the processor may need to be calibrated to adjust for the offset distance of the first sensor 32.

The first sensor 32 and the second sensor 20 are coupled to the processor 12. This may be accomplished by wire or wirelessly. The first sensor 32 and the second sensor 20 may be a six degree of freedom sensor configured to describe the location of each sensor in three translational axes, generally called X, Y and Z and three angular orientations, generally called pitch, yaw and roll. By locating the sensor in these reference frames, and knowing the location and orientation of each sensor, the landmark identifier 18 may be located relative to the landmark on the implant 30. In one particular embodiment, the information from the sensors allows for a surgeon to plan the surgical path for fixation and properly align a drill with a blind fixation hole. In the depicted embodiment, the sensors 32, 20 are six degrees of freedom sensor from Ascension Technology Corporation of 107 Catamount Drive, Milton Vt., U.S.A.; Northern Digital Inc. of 103 Randall Drive, Waterloo, Ontario, Canada; or Polhemus of 40 Hercules Drive, Colchester Vt., U.S.A. Of course, other sensors may be used.

The first sensor 32 may be attached to the implant 30. For example, the first sensor 32 may be attached to an outer surface 37. In the embodiment depicted in FIG. 1, the implant 30 may also include a groove 34 and a pocket 36 (best seen in FIG. 2). The groove 34 and pocket 36 are located in a wall of the implant 30. In the depicted embodiment, the first sensor 32 is intended to be attached to the implant 30 and installed in a patient for the service life of the implant 30. Further, in some embodiments, the orthopedic implant assembly 28 may include a cover 38 to cover the pocket 36 and/or the groove 34. The cover 38 may be substantially flush with the external surface 37 of the implant 30. Accordingly, in some embodiments, the implant 30 may include a second opening 39 (best seen in FIG. 2) to receive the cover 38.

The first sensor 32 may be tethered to leads for communication and power. The leads, and the sensor, may be fixed to the implant 30. A lead 50 may be used to connect the first sensor 32 to the processor 12 or the control unit. The lead 50 may be made from biocompatible wire. As an example, the lead 50 may be made of DFT wire available from Fort Wayne Metals Research Products Corp., 9609 Indianapolis Road, Fort Wayne, Ind. 46809. DFT is a registered trademark of Fort Wayne Metals Research Products Corp. A first connector 52 may be used to place the lead 50 relative to the implant 30. A second connector 54 may be used to connect the lead 50 to another device, such as the processor 12, the control unit, or the insertion handle 40.

The first sensor 32 may be fixed in the pocket 36 using a range of high stiffness adhesives or polymers including epoxy resins, polyurethanes, polymethyl methacrylate, polyetheretherketone, UV curable adhesives, silicone, and medical grade cyanoacrylates. As an example, EPO-TEK 301 available from Epoxy Technology, 14 Fortune Drive, Billerica, Mass. 01821 may be used. The lead 50 may be fixed in the groove in a similar manner. These types of fixation methods do not adversely affect the performance of the electrical components. Thereafter, the cover 38 may be placed on the implant 30 and welded in-place. For example, the covers may be laser welded to the implant.

The monitor 14 may be configured to display the position and orientation of the first sensor 32 and the second sensor 20 so that the display may show a surgeon both sensor positions and orientations relative to one another. The processor 12 may send positional data, either by wire or wirelessly, to a user interface, which may graphically display the relative positions of the landmark identifier and the implant on the monitor. The view displayed on the monitor 14 may be oriented relative to the landmark identifier so that the surgeon may visualize the user interface as an extension of the landmark identifier. The user interface also may be oriented so that the surgeon may view the monitor simultaneously with the surgical field.

The insertion handle 40 may be used for installation of the orthopedic implant assembly 28 and also may be used to route the leads from the first sensor 32. For example, the insertion handle 40 may route both communication and power leads between the implant 30 and the processor 12.

In the embodiment depicted in FIG. 1, the landmark identifier 18 and the insertion handle 40 each include a communications module 21, 25 for wirelessly transmitting data from the sensor 20, 32 to the processor 12, but those skilled in the art would understand that other methods, such as by wire, may be used. In the depicted embodiment, the second connector 54 plugs into the communications module 25. Alternatively, and as is explained in greater detail below, the implant 30 and the insertion handle 40 may have mating electrical contacts that form a connection when the components are assembled such that the first sensor 32 is coupled to the communications module 25.

In some embodiments, the implant 30 may include a communications circuit and an antenna for wireless communication. Power for the first sensor 32 and/or the communications circuit may be positioned within the insertion handle 40. For example, a battery may be placed within the insertion handle 40 for transferring power to the first sensor 32 and/or other electronics. Alternatively, the communications circuit, the antenna, and the battery may be located within the insertion handle 40 and each of these may be tethered to the first sensor 32. In yet another embodiment, the implant 30 may include a coil to inductively power the communications circuit and communicate data from the first sensor 32. The power source may be a single source mode or may be a dual mode AC/DC.

In use, the orthopedic implant assembly 28 is installed in a patient. For example, in the case of internal fixation, the intramedullary nail is placed within an intramedullary canal. Optionally, the user may use transfixion elements, such as screws, to first lock the proximal end of the intramedullary nail. An operator uses the targeting device 18 and the first sensor 32 to identify the landmarks 31. For example, in the case of intramedullary nail fixation, a surgeon uses the targeting device 18 to identify the blind transfixion holes and drill through the holes for placement of a transfixion element.

Figure 2:
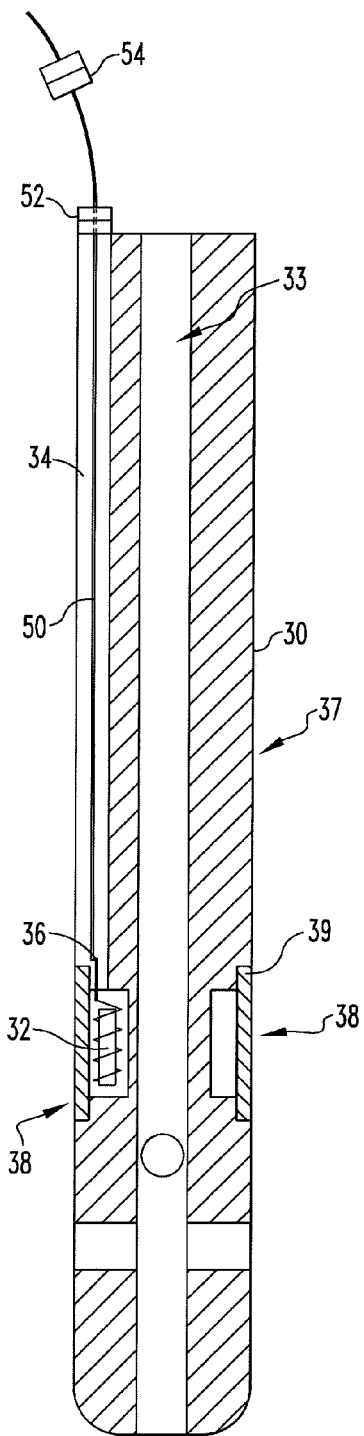
FIG. 2 is a sectional view of the orthopedic implant assembly shown in FIG. 1.

FIG. 2 further illustrates the implant 30 as shown in FIG. 1. The implant 30 may include the first sensor 32, the longitudinal groove 34, the pocket 36, the cover 38, and the second opening 39. As examples, the cover 38 may be comprised of gold or titanium foil. In some embodiments, the implant 30 may include an inner surface 35 that forms a cannulation 33. The implant 30 may include the outer surface 37.

Figure 3:
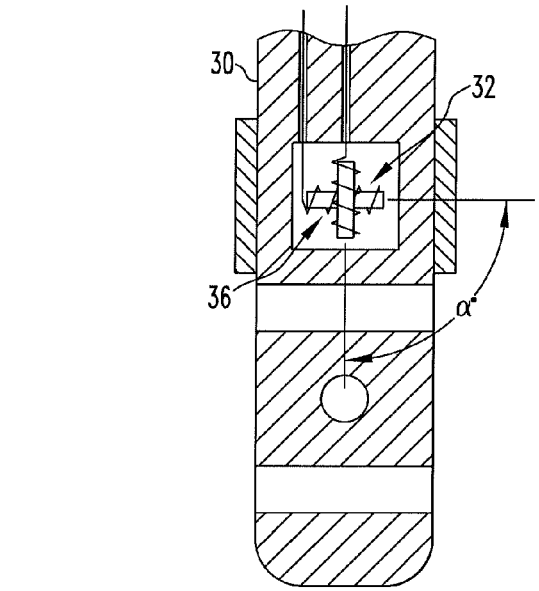
FIG. 3 illustrates a sensor mounting for the orthopedic implant assembly illustrated in FIGS. 1-2.

FIG. 3 illustrates a first embodiment of the first sensor 32. The first sensor 32 may include two coils cross-layered to one another and having an angle alpha.

Figure 4:
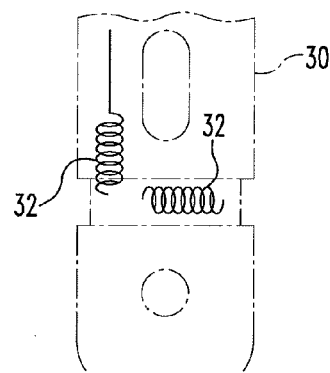
FIG. 4 illustrates another disclosed sensor mounting for the orthopedic implant assembly illustrated in FIGS. 1-2.
Figure 5:
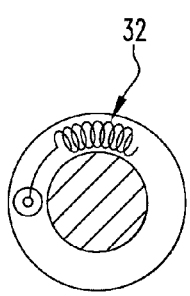
FIG. 5 illustrates the sensor shown in FIG. 4.

FIGS. 4 and 5 illustrate a second embodiment of the first sensor 32. The first sensor may include two coils generally orthogonal to one another in order to establish the orientation and position in the six degrees of freedom. A first coil may be oriented along the length of the implant 30. The second coil may be oriented either wrapped around the circumference of the implant, for example in a groove, or along the radius of the implant 30. In addition, while it is preferred to have the coils perpendicular to one another, other orientations may be used, although the mathematics may be more complex. Further, the coils may be oriented spirally around the implant 30. Such an orientation may allow two coils to be placed perpendicular to each other with both coils placed along both the length of the implant and along the circumference of the implant 30.

Figure 6:
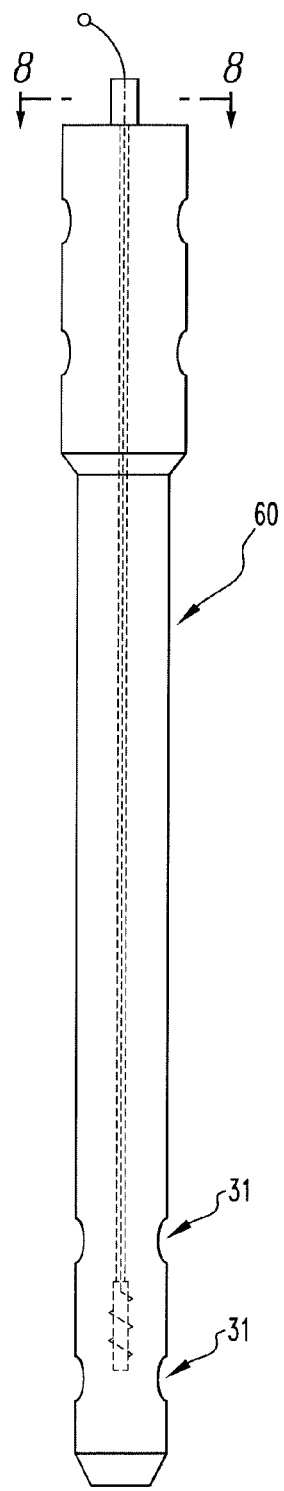
FIG. 6 illustrates another disclosed orthopedic implant assembly.
Figure 7:
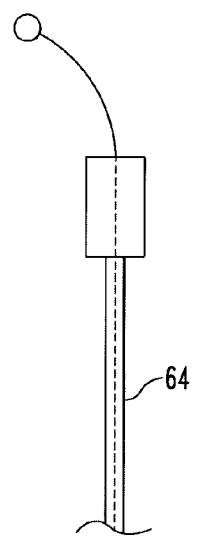
FIG. 7 is a front view of a removable lead for the orthopedic implant assembly illustrated in FIG. 6.
Figure 8:
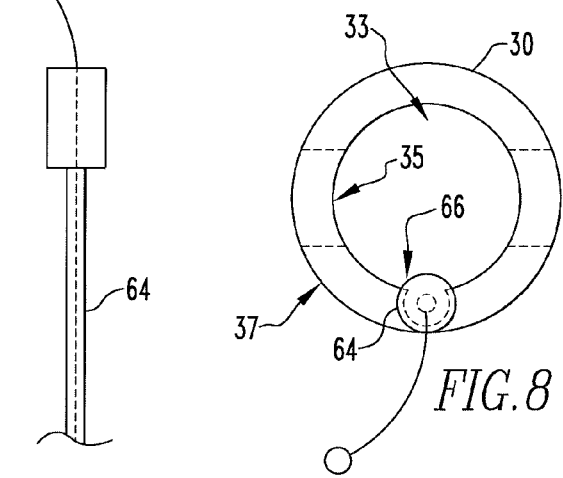
FIG. 8 is a top view of the orthopedic implant assembly shown in FIG. 6.

FIGS. 6-8 illustrate a second embodiment of the orthopedic implant assembly 60. The orthopedic implant assembly 60 may include the implant 30. In the embodiment depicted in FIG. 6, the implant 30 may include landmarks in the form of transfixion holes 31. The implant 30 may include a longitudinal internal groove 66 and a removable lead 64. In the embodiment depicted in FIG. 8, a diameter of the longitudinal groove 66 is shown as intersecting with the cannulation 33; however, in other embodiments, the diameter of the longitudinal internal groove is contained between the outer surface 37 and the inner surface 35. The removable lead 64 may include the first sensor 32 at its distal end portion 65. The first sensor 32 is located a known offset from the landmarks 31. The implant in FIGS. 6-8 is comprised of biocompatible material, and may be a metal alloy or a polymer. The longitudinal groove 66 may be machined or molded in place.

In use, the implant 30 with the removable lead is installed in a patient. For example, in the case of internal fixation, the intramedullary nail is placed within an intramedullary canal. Optionally, the user may use transfixion elements, such as screws, to first lock the proximal end of the intramedullary nail. Because of the location of the longitudinal groove 66, the removable lead 64 does not interfere with first locking the proximal end of the intramedullary nail. An operator uses the targeting device 18 and the first sensor 32 to identify the landmarks 31. For example, in the case of intramedullary nail fixation, a surgeon uses the targeting device 18 to identify the blind transfixion holes and drill through the holes for placement of a transfixion element. After the implant 30 is secured, the operator removes the removable lead 64 and it may be discarded.

Figure 9:
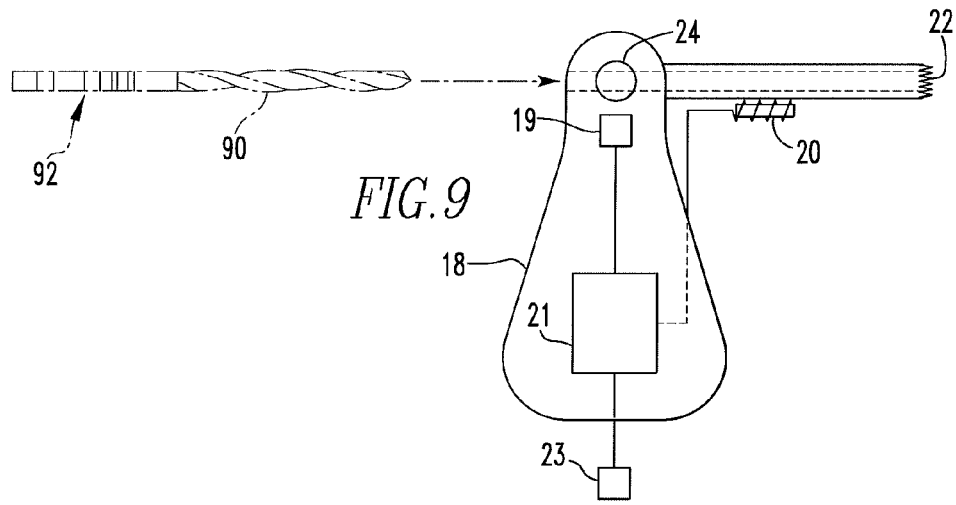
FIG. 9 illustrates a landmark identifier as disclosed in FIG. 1.
Figure 32:
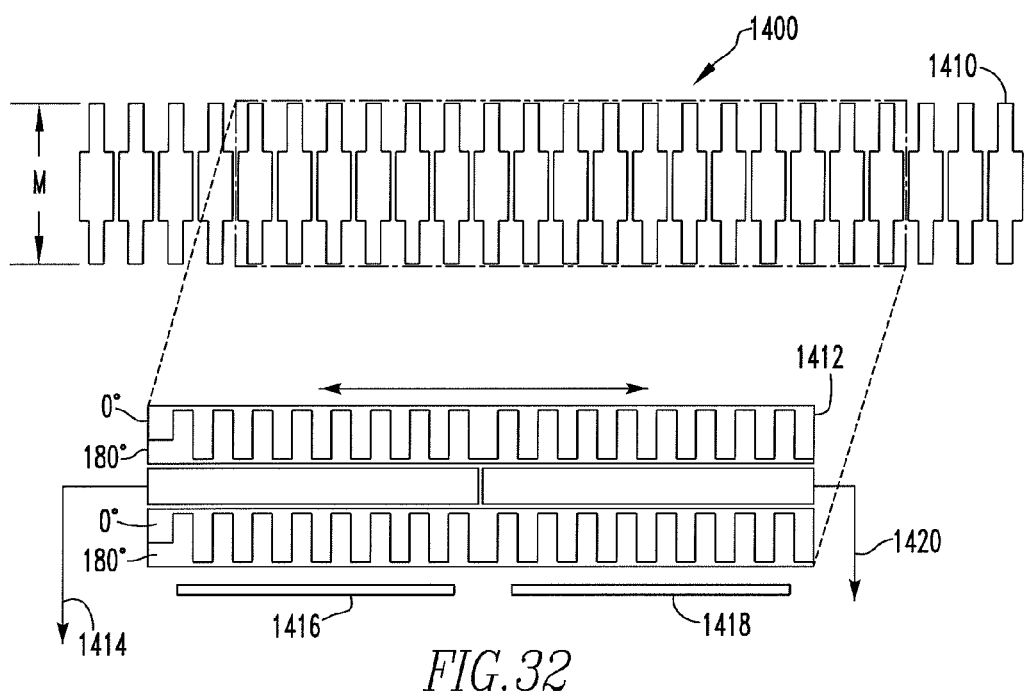
FIG. 32 illustrates a disclosed device for tracking drill depth.

FIG. 9 one particular embodiment of the landmark identifier 18 as shown in FIG. 1. In the depicted embodiment, the landmark identifier 18 may include the sensor 20, the serrated tip 22, the tube 24, and the handle 26. A drill 90 has markings 92 that interact with a marking sensor 19 adjacent the tube 24. The interaction is similar to a pair of digital measuring calipers in that the position between marking 92 and sensor 19 equate to a distance. This distance can be used to determine the depth of the drill into the bone and ultimately the length of the bone screw that will be inserted into the drilled hole. Distance, or drill depth, readings are only obtainable when the sensors 92 and 19 are in close proximity to each other, i.e. the drill 90 is inside the tube 24. Exemplary measurement devices are shown in U.S. Pat. No. 6,675,491 issued on Jan. 13, 2004 to Sasaki et al. and in U.S. Pat. No. 7,253,611 issued on Aug. 7, 2007 to Me et al., each of which is incorporated by reference. In the depicted embodiment, the marking sensor 19 is coupled to the communications module 21. Alternatively, the marking sensor 19 may be connected by wire to the processor 12. In FIG. 9, the communications module 21 may include a third connector 23 for electrical connection to the processor 12. Additional embodiments of the landmark identifier are shown in FIGS. 32-34.

Figure 9A:
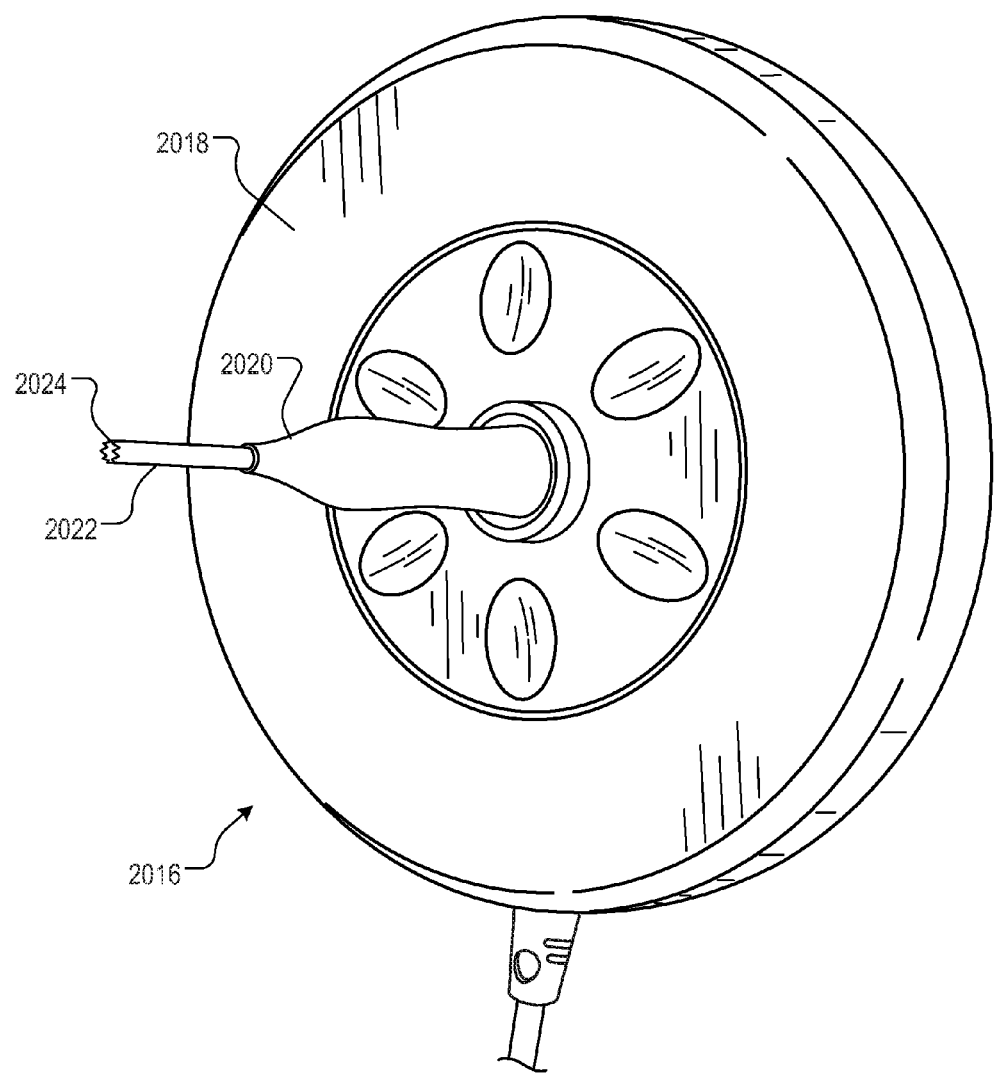
FIG. 9A illustrates another disclosed landmark identifier that is contained within a common housing with field generator and that may be hand-held.

FIG. 9A illustrates an embodiment combining a landmark identifier and a field generator. In the exemplary embodiment, the handheld landmark identifier 2016 houses an electromagnetic field generator (not shown) which includes one or more induction coils or other elements mounted in or on a preferably autoclavable material and encapsulated in a preferably silicone housing body 2018 to create a suitable electromagnetic field or fields. Such coils or elements can be oriented and disposed in the landmark identifier 2016 in a manner that is conventional in the art. The relative orientation and position of the induction coils or elements in the landmark identifier 2016 are preferably selected to optimize the balance between the qualities and strength of the electromagnetic field or fields and their interaction with the sensor and the weight, size, form factor and ergonomics of the identifier 2016. Preferably at least three induction coils are mounted in or on the autoclavable material. The particular landmark identifier 2016 shown in FIG. 9A further includes a removable sleeve attachment 2020, a sleeve 2022, and a serrated tip 2024, though different components and constructions can be included as mentioned elsewhere in this document (see, for example, ¶82 above). The sleeve attachment 2020 and the sleeve 2022 can be formed as a single unit or as separate units coupled to each other by adhesives or other connection means known to one skilled in the art. For illustration purposes, the sleeve 2022 as shown in FIG. 9A is a drill sleeve, but it can also be a larger size sleeve such as a screw driver sleeve or other sleeves as selected by the surgeon, or other components as disclosed, for example, in ¶85 above. To change sleeves or other components, the surgeon unscrews the sleeve attachment and replaces it with another sleeve attachment of choice and its corresponding sleeve.

Unlike the landmark identifier 18 shown in FIG. 9, the landmark identifier 2016 depicted in FIG. 9A does not require the second sensor 20 as shown in FIG. 9 since the origin of the global space (the area in which the electromagnetic field is generated) can be defined within the landmark identifier 2016. One axis of the global space co-ordinate system can be the longitudinal axis of the drill sleeve or other component 2022. In that event, the other two axes of the global space co-ordinate system can be defined by planes orthogonal to that longitudinal axis and to each other. Advantages of incorporating the field generator into the landmark identifier 2016 include a smaller size field generator because it can be brought into the local working space (area which includes the landmarks such as implant holes that are to be targeted for screw placement) therefore requiring a smaller electromagnetic field. The global space and local working space become the same or at least correspond more closely spatially when the landmark identifier 2016 with its field generator brought into the vicinity of the landmark, implant or probe sensor (not shown). Since the electromagnetic field size requirement is smaller, the induction coils within the field generator can be smaller which therefore reduces the size and weight of the handheld field generator to make it more manageable for handheld usage.

The material selection for the landmark identifier 2016 which houses the field generator can be optimized for weight and stability after multiple autoclave cycles. Any autoclavable material can be used, and the materials are preferably non-magnetic or weak magnetic to avoid or minimize interference with the electromagnetic fields. Exemplary materials include ceramic, CoCr, plastic or combinations thereof.

Figure 10:
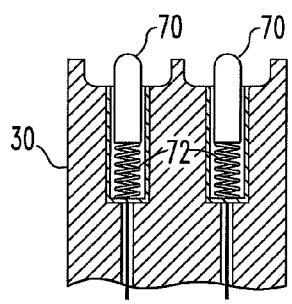
FIG. 10 is a sectional view illustrating disclosed point contacts for the orthopedic implant assembly illustrated in FIGS. 1-2.
Figure 11:
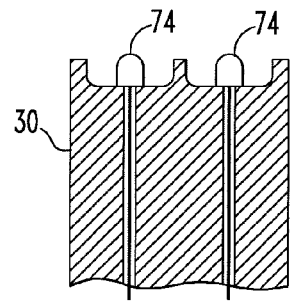
FIG. 11 is a sectional view illustrating additional disclosed point contacts for the orthopedic implant assembly illustrated in FIGS. 1-2.
Figure 12A:
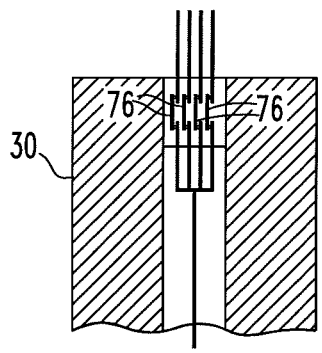
FIG. 12A is a sectional view illustrating a disclosed crimp electrical connection for the orthopedic implant assembly illustrated in FIGS. 1-2.
Figure 12B:
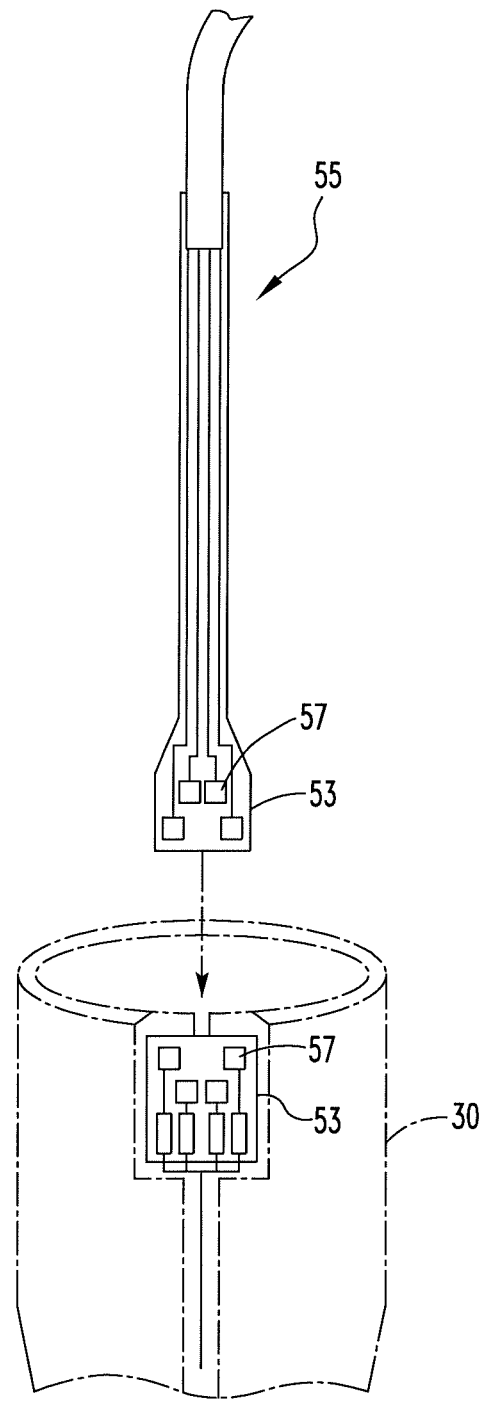
FIG. 12B is a schematic view illustrating another disclosed electrical connection for the orthopedic implant assembly illustrated in FIGS. 1-2.
Figures 12C, 12D:
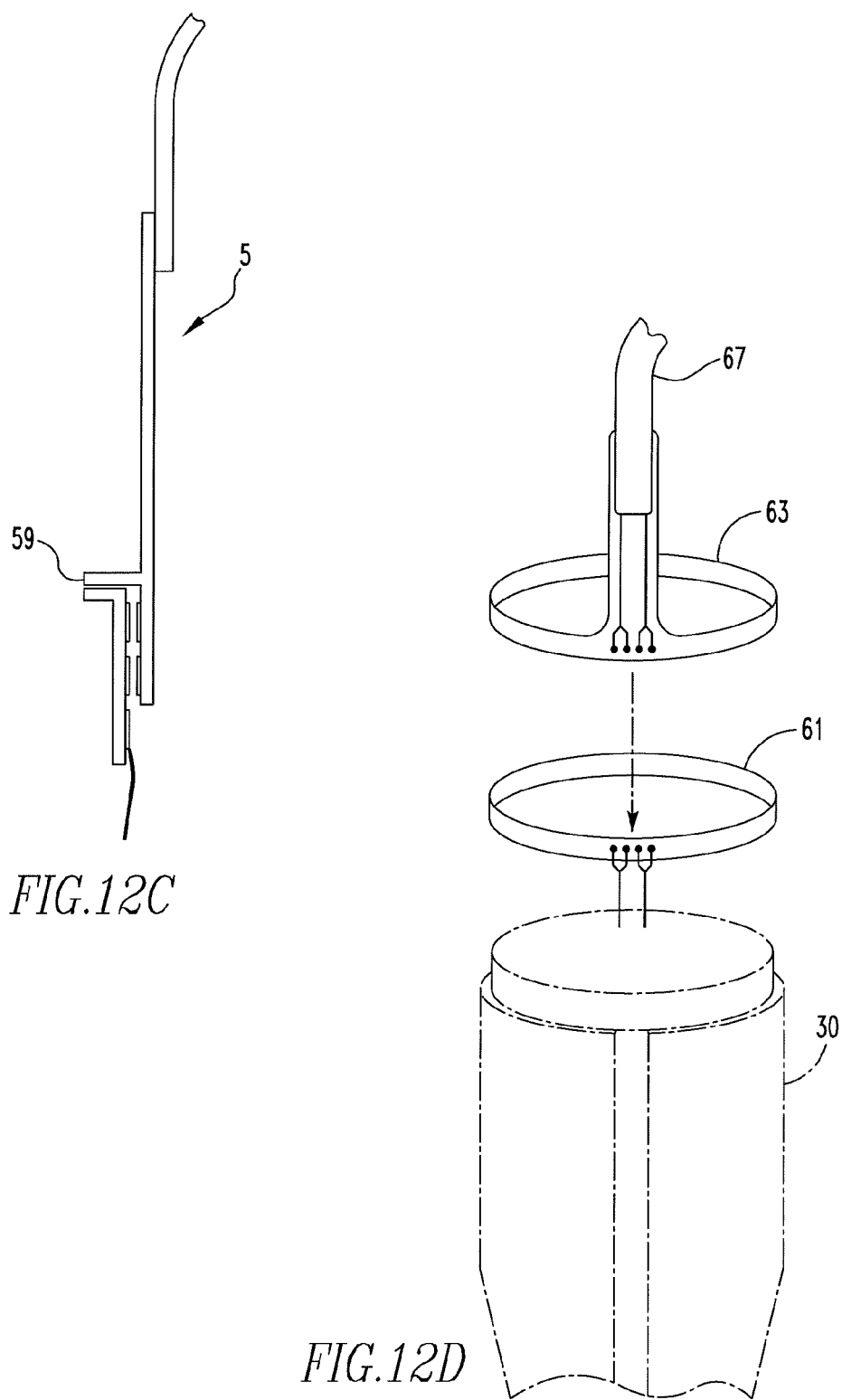
FIG. 12C is a schematic view illustrating a side view of the electrical connection shown in FIG. 12B.
FIG. 12D is an exploded view illustrating yet another disclosed electrical connection.

FIGS. 10-12 illustrate exemplary methods of electrically connecting the implant 30 to the insertion handle 40, which has corresponding electrical contacts. In FIG. 10, biasing elements 72 bias contacts 70 toward the insertion handle 40. In FIG. 11, the implant 30 has elastomeric electrical contacts 74. In FIG. 12A, wires extending between the lead 50 and another component are crimped together at junction 76. In one method, the wires are torn free and separated at the junction 76 after installation of the orthopedic implant assembly 28. In yet another method, the wires are cut above the junction 76 after installation of the orthopedic implant assembly 28. In FIGS. 12 B and C, two flex boards 53 are soldered together one or more pads 57 to connect a wiring harness 55 to the sensor. The wire harness 55 may be mounted to the insertion handle 40 or within a cannulation of the insertion handle 40. In the depicted embodiment, four pads 57 are soldered together. Locking tabs 59 are sandwiched between the implant 30 and the insertion handle 40 to withstand abrasion and tension associated with the implant insertion. Once the insertion handle is removed, the wire harness 55 can be pulled such that all non-biocompatible materials are pulled with it. In FIG. 12D, rings 61, 63 are connected during manufacturing. After implantation, both rings 61, 63 are removed by pulling on a jacketed wire 67.

Figure 13A:
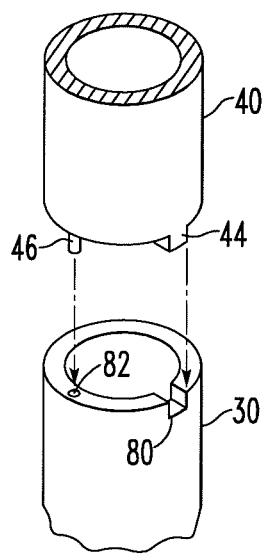
FIG. 13A is a partial perspective and exploded view illustrating another mechanism for aligning the orthopedic implant and the insertion handle.

Referring now to FIGS. 13A and B, the implant 30 and/or the insertion handle 40 may include one or more alignment features 44 and mating notch 80 or alignment pin 46 and mating hole 82. The insertion handle may be configured to align with an upper surface of the implant. In one embodiment, the insertion handle may have a key configured to mate to a slot on the implant. Other alignment guides may be used. In addition, the guide may have an electrical connector configured to mate to an electrical connector on the implant. The connection between the guide and the implant may be spring loaded to ensure electrical contact between the electrical connectors. In order to avoid shorting the connection between the guide and the implant, the electrical connector may be insulated. As another example of electrically connecting the insertion handle to the implant, the electrical connectors may include a post and slip rings. The rings may be located on the implant, and the posts located on the insertion handle. The posts are biased to contact the rings. In such an embodiment, the angular location of the insertion handle relative to the axis of the implant is not fixed. This would allow the insertion handle to be positioned to the implant irrespective of angular position.

Figure 13B:
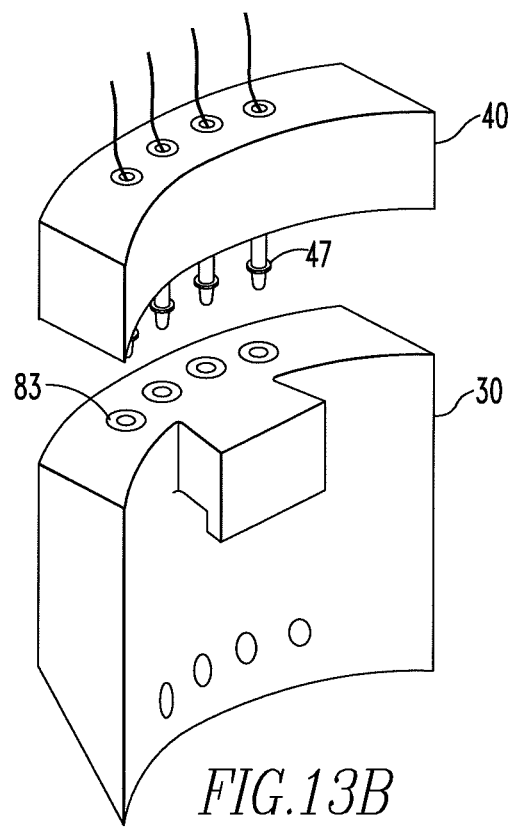
FIG. 13B is a partial perspective and exploded view illustrating another mechanism for aligning the orthopedic implant and the electrical connection.

In another embodiment shown in FIG. 13B, the implant 30 and/or the insertion handle 40 may include one or more alignment pin 47 and mating hole 83. The alignment pins 47 may be spear tip pins designed to engage a single time and when removed, the pins grip portion of the implant to remove all non-biocompatible materials with them.

Figure 14:
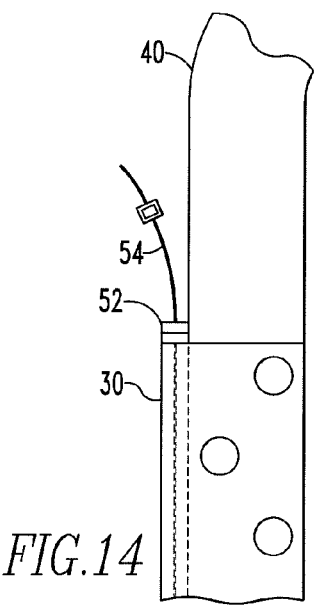
FIG. 14 illustrates one disclosed connection between the insertion handle and the orthopedic implant.

Any of the electrical connectors above may include a memory storage device (not shown) for storing offset values for sensor calibration. Referring now to FIG. 14, the implant 30 and the insertion handle 40 may be sized such that space remains available for the first connector 52 even when the components are assembled or mated.

As an example, the system for identifying landmarks may be used to target blind screw holes of an implanted intramedullary nail. The intramedullary nail is implanted in the patient. The electromagnetic field generator is activated. The processor receives signals from the sensor mounted to the intramedullary nail and from the sensor mounted to the landmark identifier, such as a drill sleeve. A computer program running on the processor uses the information of the at least two sensors and graphically display them in relative position on the monitor. A surgeon moves the landmark identifiers into position using feedback provided by the processor. When the landmark identifier is in the proper location, the surgeon drill through bone and the intramedullary nail to create a screw hole. In some embodiments, the processor may provide feedback as to the depth of the drilled hole. The surgeon may then place a screw through the drilled hole to affix the blind hole of the intramedullary nail.

FIG. 15 illustrates another disclosed system 110 for identifying landmarks. The system 110 may include a processor 112, a landmark identifier 118, and an orthopedic implant assembly 128. In some embodiments, the system 110 may also include a monitor 114 and an insertion handle 140.

The landmark identifier 118 is used to target a landmark. The landmark identifier 118 may include a second sensor 120. In the embodiment depicted in FIG. 15, the landmark identifier 118 is a drill sleeve with a serrated tip 122, a tube 124, and a handle 126. In the depicted embodiment, the second sensor 120 is oriented relative to an axis of the tube, which may receive a drill. This offset of the sensor from the tube allows the position of the tube to be located in space in six dimensions (three translational and three angular) relative to the transmitter or another sensor in the system. In some embodiments, the processor may need to be calibrated to adjust for the offset distance of the second sensor 120.

The orthopedic implant assembly 128 may include an implant 130 and a magnet 132. The magnet may be a permanent magnet or an electromagnet. The magnet 132 is oriented in a predetermined position relative to a landmark on the orthopedic implant 130. This offset of the magnet from the landmark allows the position of the landmark to be located in space in six dimensions (three translational and three angular) relative to the transmitter or another sensor in the system, such as the second sensor. In some embodiments, the processor may need to be calibrated to adjust for the offset distance of the magnet 132. In the embodiment depicted in FIG. 1, the implant 130 may also include a pocket 136 and a cover 138. In the case of an electromagnet, a lead 150 connects to the magnet 132 and is contained within a groove 134.

As an example, the system for identifying landmarks may be used to target blind screw holes of an implanted intramedullary nail. The intramedullary nail is implanted in the patient. The processor receives signals from the sensor mounted to the landmark identifier, such as a drill sleeve. A computer program running on the processor uses the information of the sensor and graphically displays the sensor in relative position to the magnet on the monitor. A surgeon moves the landmark identifiers into position using feedback provided by the processor. When the landmark identifier is in the proper location, the surgeon drill through bone and the intramedullary nail to create a screw hole. In some embodiments, the processor may provide feedback as to the depth of the drilled hole. The surgeon may then place a screw through the drilled hole to affix the blind hole of the intramedullary nail.

Figure 16:
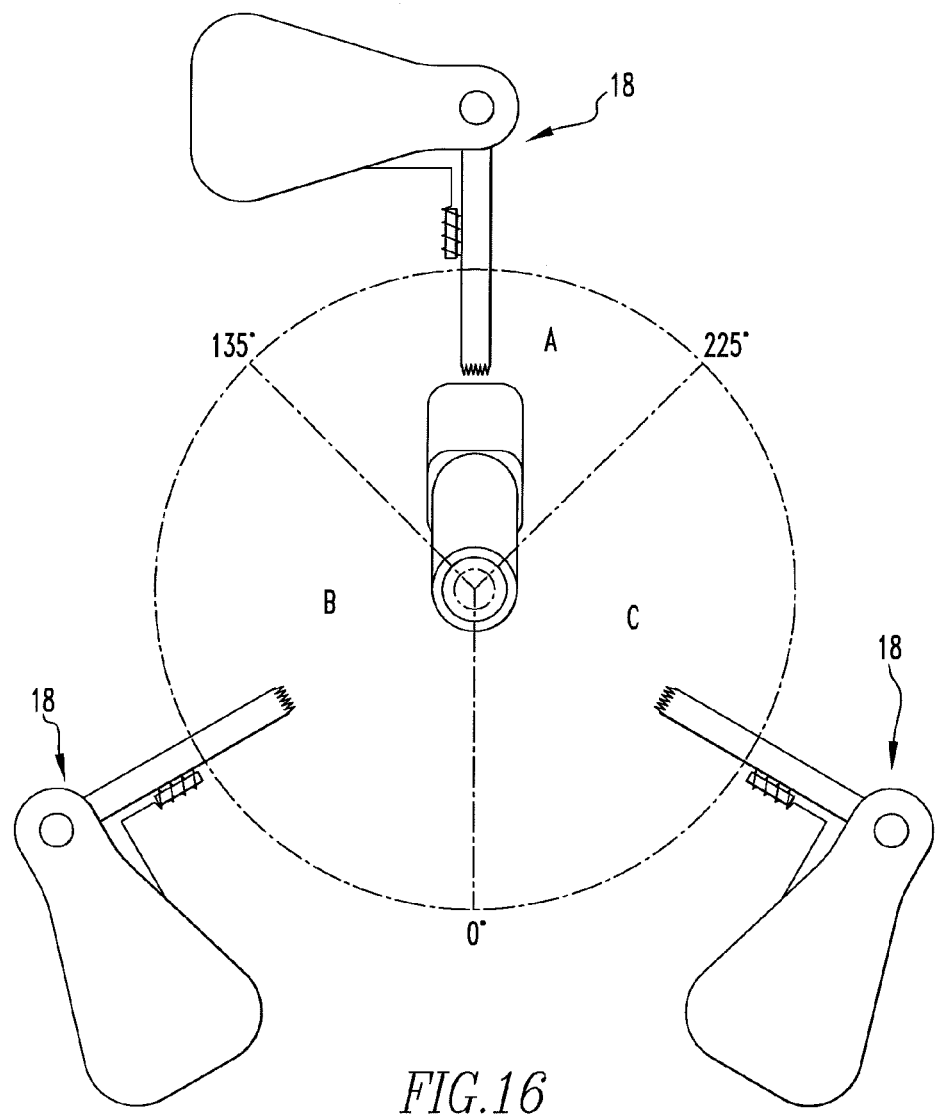
FIG. 16 is a schematic illustration of view selection criteria.

FIG. 16 illustrates a method for selecting views corresponding to landmark identifier position. In some embodiments, the view displayed on the monitor is dependent upon the location of the landmark identifier relative to the implant. The diameter of the implant is broken into sectors or fields. In the embodiment depicted in FIG. 16, the diameter is broken down into three fields: (A) 135 degrees to 225 degrees; (B) 0 degrees to 135 degrees; and (C) 225 degrees to 360 degrees. The initial view is based upon landmark identifier orientation relative to the implant. As the user moves landmark identifier toward or away from the implant, the monitor display zooms in or out on the selected field.

Figure 17:
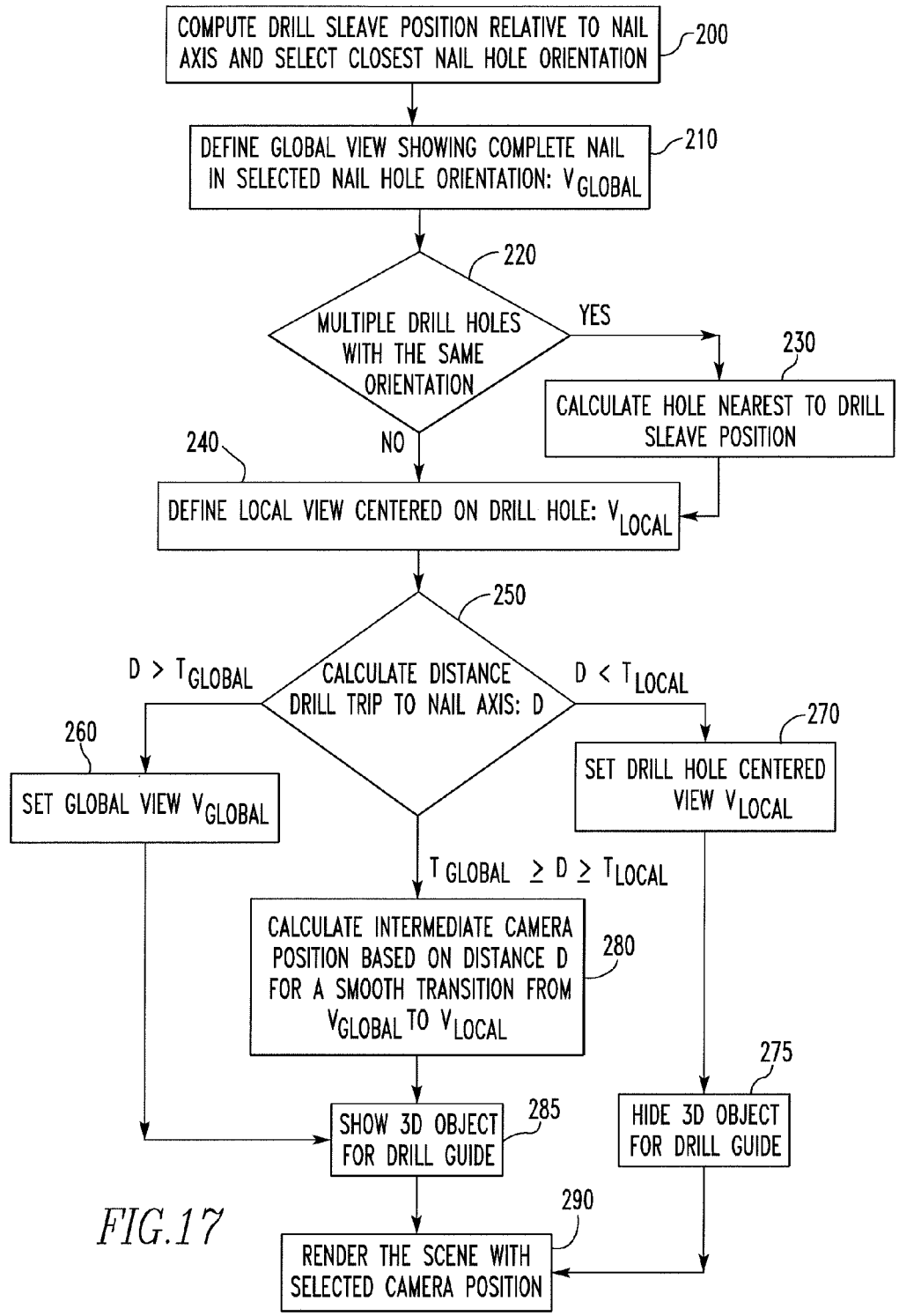
FIG. 17 is a flowchart illustrating the step of view selection.

FIG. 17 is a flowchart for view selection and display of one landmark. The process may be repeated for multiple landmarks. The processor 12 uses the transformation matrix in the following process steps. In step 200, landmark identifier position is computed relative to the implant based upon the positions of the relevant sensors, and the landmark closest the landmark identifier is selected for display. In step 210, a global view is defined showing the whole implant with the selected landmark oriented for proper viewing. A global view is analogous to viewing the implant at a distance. In step 220, there is a decision whether there are multiple landmarks having the same orientation. If yes, then in step 230, the processor calculates which landmark is nearest to the landmark identifier position and selects it for viewing. If no, in step 240, a local view is defined and centered upon the selected landmark. A local view is analogous to viewing the implant in close proximity. In some embodiments, it may be desirable to hide the landmark identifier when the local view is defined. In steps 250, 260, and 270, the processor 12 identifies the distance from landmark identifier to the landmark and depending upon the decision made, either hides or renders the landmark identifier. In step 250, the distance from landmark identifier to the landmark and a comparison is made between the calculated distance D and set variables $T_{Global}$ and $T_{Local}$. If $D>T_{Global}$, then the global view is selected in step 260 and the processor proceeds to step 285. If $D<T_{Local}$, then the local view is selected and centered upon the landmark in step 270. Thereafter, the processor proceeds to step 275. In optional step 275, the landmark identifier is hidden. Otherwise, an intermediate camera position is calculated based upon the distance D to enable a smooth transition from global view to a local view in step 280. In step 285, the landmark identifier is shown. In step 290, the scene with selected camera position is rendered.

Figure 18:
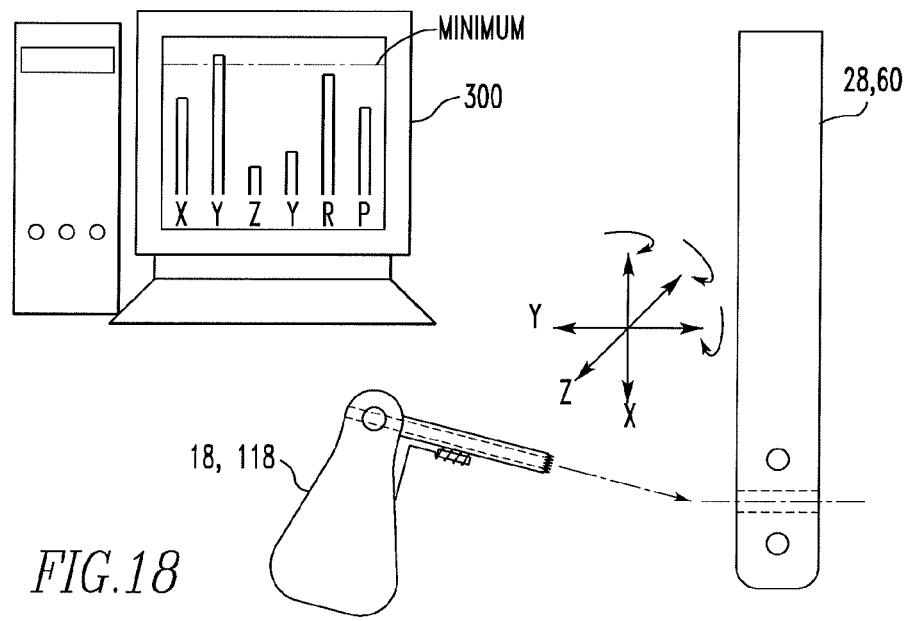
FIG. 18 is a schematic illustrating a disclosed method of aligning a landmark identifier.

FIG. 18 is a schematic illustrating a first alternative method of aligning the landmark identifier. A computer program running on the processor may be used to take the information of the at least two sensors and graphically display them in relative position (the second sensor relative to the first sensor) on the monitor. This allows the user to utilize the system to guide the placement of the landmark identifier. In the case of drilling a blind intramedullary nail hole, the system guides the user in placement of the drill sleeve and subsequently drilling accurately thru the hole in the intramedullary nail. The graphical user interface may include an alignment guide for each of the degrees of freedom. A minimum alignment level may be set such that the surgeon continues to orient the landmark identifier until each of the degrees of freedom meets the minimum alignment level for an effective placement of the landmark identifier. The example of FIG. 18 shows an instance where the placement in the Y-direction meets the minimum required tracking placement. However, none of the other translational or rotational degrees of freedom meet the minimum requirements. While the magnitudes of tracking are shown as bar graphs, other graphical representations, such as color coding, may be used.

Figure 19:
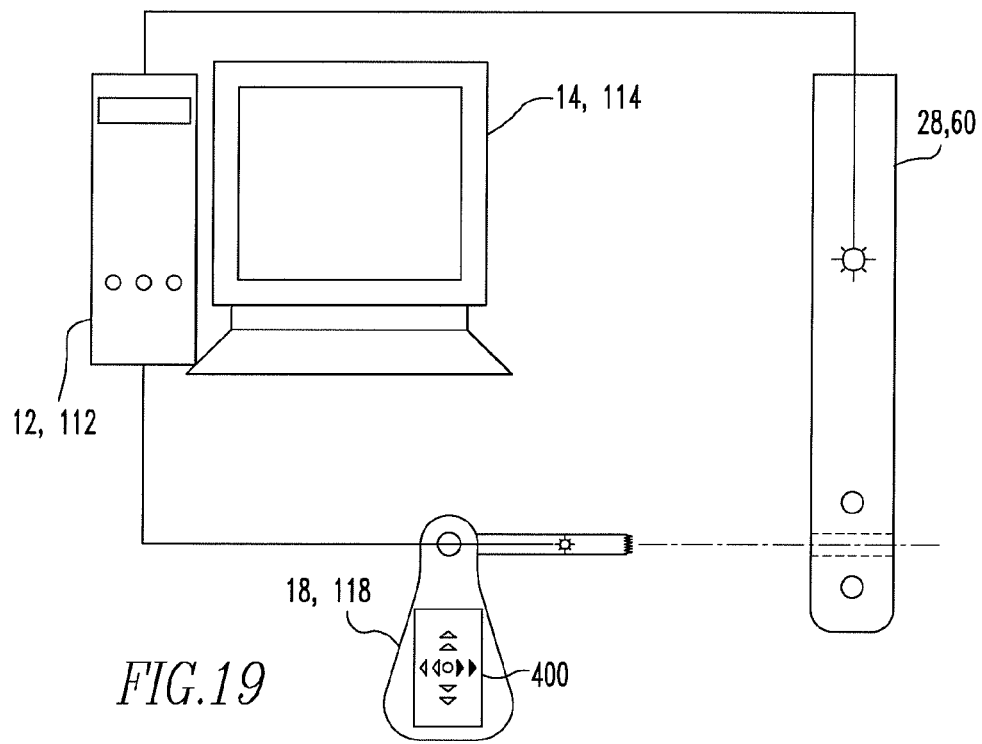
FIG. 19 is a schematic illustrating a disclosed method of aligning a landmark identifier.

FIG. 19 is a schematic illustrating a second alternative method of aligning the landmark identifier. In this embodiment, a graphical interface using a plurality of LEDs to position the drill may be placed upon the landmark identifier, such as a drill sleeve. By using the LEDs to trajectory track the drill, the surgeon may align the drill with the blind fixation hole. The trajectory may additionally use secondary displays to add more information to the system. For example, for affecting the magnitude of adjustment, the trajectory may include flashing LEDs so that high frequency flashing requires larger adjustments while low frequency flashing may require smaller adjustments. Similarly, colors may add information regarding adjustments to alignment.

Figure 20:
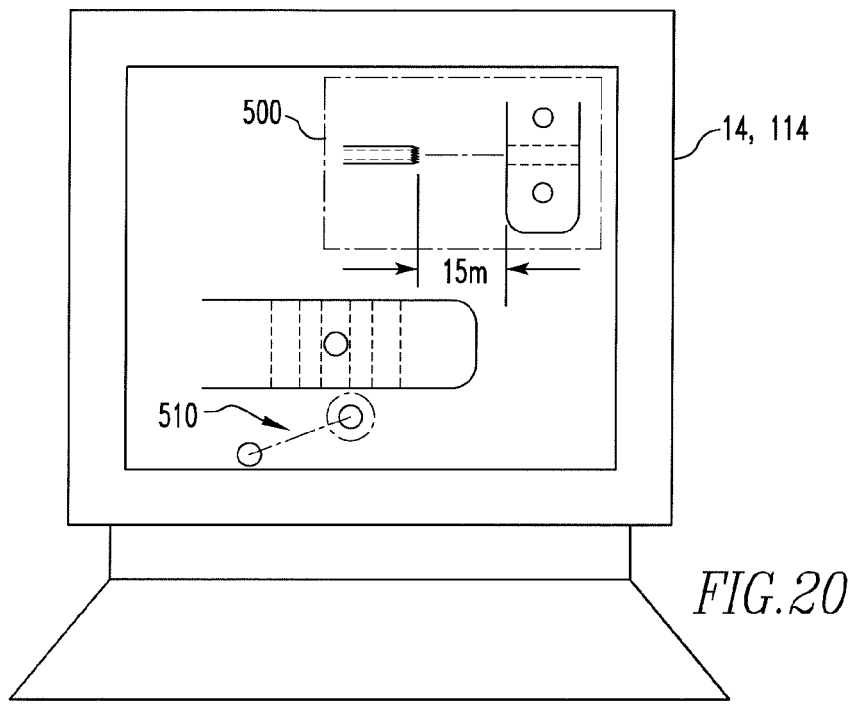
FIG. 20 illustrates a monitor with exemplary views.

FIG. 20 illustrates a monitor with exemplary views. A first portion 500 indicates the distance the drill is on each side of the implant. This may provide the user with a better understanding of drill depth and alert the user when to stop when appropriate drill depth has been achieved. The second portion 510 provides the user with alignment information. As an example, drill depth data may be obtained using the embodiment shown in FIG. 9.

Figure 21:
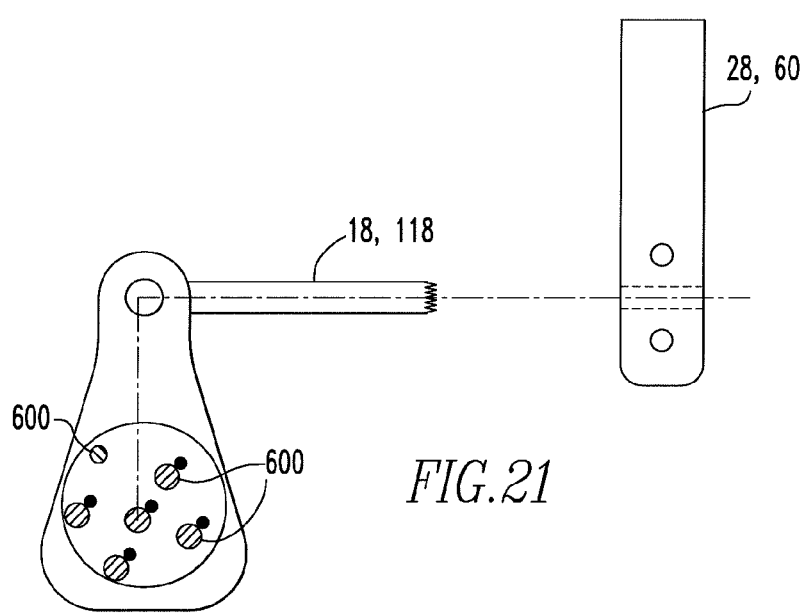
FIG. 21 illustrates another disclosed landmark identifier.

FIG. 21 illustrates another landmark identifier. The landmark identifier is configured to display, with LEDs, the position and trajectory information for proper alignment. The size of the LEDs may display additional information regarding the magnitude of required adjustment. The trajectory light may display a simple on/off toggle between an aligned trajectory and a mal-aligned trajectory. As another example, the trajectory LED may be color coded to suggest the magnitude of necessary adjustment for proper alignment.

Figure 22:
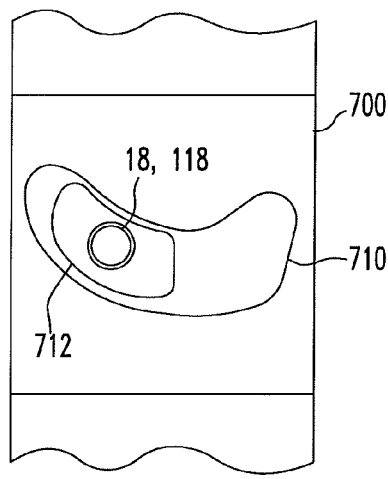
FIG. 22 is a partial view of another disclosed insertion handle.

FIG. 22 illustrates another disclosed insertion handle 700. The insertion handle 700 may include an arcuate slot 710. The arcuate slot limits the movement of the landmark identifier 18, 118 within the operating space. In the case of identifying a blind screw hole, the arcuate slot limits the movement of the drill sleeve for fine adjustment of its position. In some embodiments, the insertion handle 700 may include a carriage 712 that receives the landmark identifier and rides in the slot 710.

Figure 23:
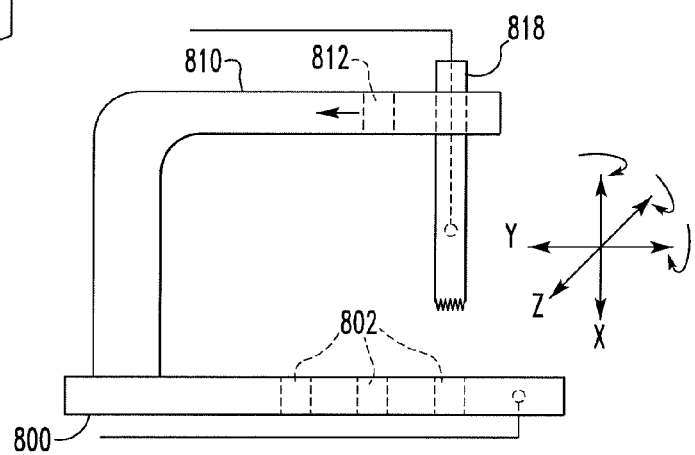
FIG. 23 illustrates another disclosed system for identifying landmarks.

FIG. 23 illustrates another system for identifying landmarks. In this embodiment, the orthopedic implant 800 is a bone plate and the insertion handle 810 is a guide affixed to the bone plate. In the depicted embodiment, the inductive sensor is placed on the surface of the orthopedic implant 800 relative to one or more landmarks. The guide 810 may allow a landmark identifier 818 to translate and/or rotate relative to the guide to properly align the landmark identifier with a landmark 802, such as a fastener hole. In addition, where multiple fixation holes are on the implant, then additional guide holes 812 on the guide 810 may help approximate the position of the additional fixation holes.

Figure 24:
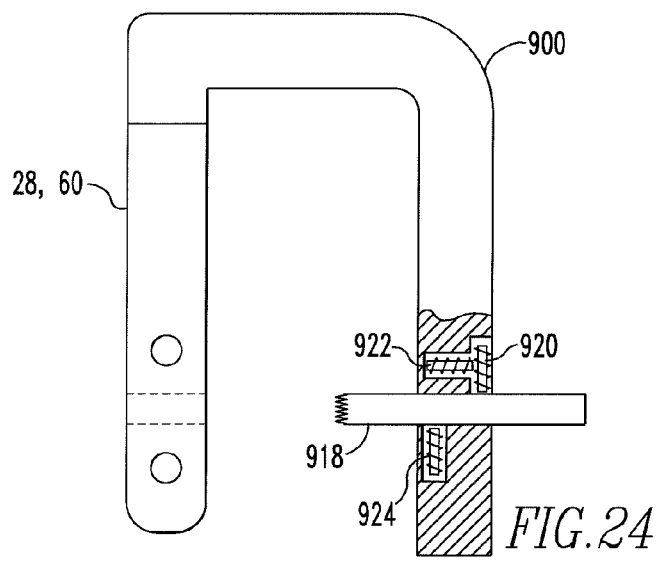
FIG. 24 is a partial view of another disclosed insertion handle.

FIG. 24 illustrates another insertion handle. The insertion handle 900 may include fine adjustment in landmark identifier 918 position through the use of small servomotors 920, 922, 924. The servomotors 920, 922, 924 may adjust the orientation and position of the landmark identifier 918. Control of the servos may be automatic or may be controlled by a surgeon.

Figure 25:
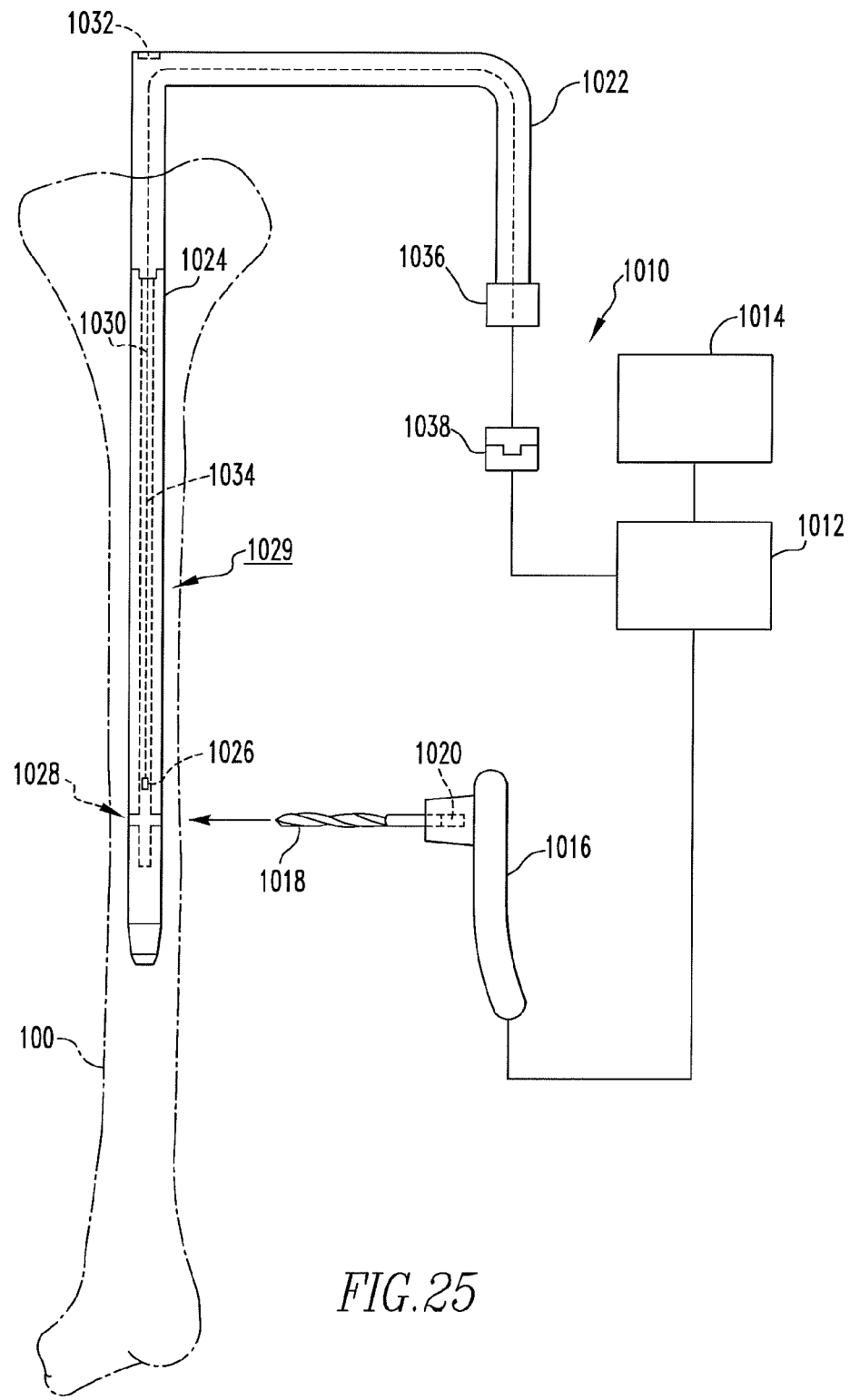
FIG. 25 illustrates yet another disclosed system for identifying landmarks.

FIG. 25 illustrates a bone 100 and a system 1010 for identifying landmarks. The system 1010 may include a control unit 1012, a field generator 1014, a landmark identifier 1016, an intramedullary nail 1024, and a probe 1029. The landmark identifier 1016 also may be referred to as a targeter. The control unit 1012 may be included as part of the processor described above or may be a separate unit. The intramedullary nail 1024 is inserted into the bone 100, and the intramedullary nail 1024 has a hole or landmark 1028. In the depicted embodiment, the field generator 1014 is electrically coupled to the control unit 1012. In the depicted embodiment, an insertion handle 1022 is removably attached to the intramedullary nail 1024. The insertion handle 1022 and/or the intramedullary nail 1024 may be cannulated. In some embodiments, the insertion handle 1022 may include a third sensor 1032.

The landmark identifier 1016 may include a second sensor 1020. The landmark identifier 1016 may guide a drill bit 1018, and the drill bit 1018 may be coupled to a drill (not shown). The second sensor 1020 may be coupled to the control unit 1012, either by wire or wirelessly. In some embodiments, the field generator 1014 may be directly mounted on the landmark identifier 1016.

The probe 1029 may include a wire 1030, a tape 1034, and a stop 1036. In the depicted embodiment, the tape 1034 is a 0.125 inch wide by 0.060 inch thick 300 series stainless steel fish tape available from Ideal Industries, Inc. of Sycamore, Ill. However, those of ordinary skill in the art would understand that other materials and other sizes may be used. For example, any narrow band of polymer, composite material, or metal may be used as the tape 1034, but it may be preferred to use a non-ferrous metal. The tape 1034 may be coiled before placement into the intramedullary nail 1024. Coiling of the tape 1034 may cause it to have a natural curvature. The tape 1034 may have, in some embodiments, a rectangular geometry that assists in orienting the tape as it is placed into a cannulation of the intramedullary nail 1024. An oval, square, or circular geometry also may be used. In some embodiments, the wire 1030 may be operatively coupled to the tape 1034. For example, this may be accomplished through the use of an adhesive or fastener. The tape 1034 may include graduations or detents to indicate a depth of the tape as it is inserted into the implant.

A first sensor 1026 is coupled to the control unit 1012, either by wire or wirelessly. In the depicted embodiment, the first sensor 1026 is connected through the use of the wire 1030 and a connector 1038. In some embodiments, the connector 1038 may be omitted. The first sensor 1026 may be coupled to a distal end of the tape 1034, and the stop 1036 may be coupled to a proximal end of the tape 1034.

In some embodiments, the probe 1029 may include a sensor housing (not shown) to house the first sensor 1026. The sensor housing may be attached to the tape 1034. The sensor housing may be made of a non-ferrous material, such as a polymer, a composite, or a metal. The sensor housing may include an appropriate strain relief to shield the wire 1030 from stresses. The sensor housing may be constructed and arranged to be large enough to hold the first sensor 1026 but small enough to fit through the cannulation of the insertion handle or the implant. Further, the sensor housing may be constructed and arranged to be long enough to allow passage through intramedullary nail bends, intramedullary nail bow, and/or bends in relevant instrumentation. Geometries of the leading and trailing faces of the sensor housing may be designed such that the sensor housing does not catch or snag on the cannulation of the instrumentation or implant.

The stop 1036 may be used to control the placement of the sensor 1026. If the tape 1034 is a fixed length and the distance is known from the end of the insertion handle to the hole 1028, repeatable placement of the first sensor 1026 may be achieved. The tape 1034 may be of sufficient length such that the sensor 1026 is aligned with the hole 1028, adjacent the hole 1028, or offset from the hole 1028.

In some embodiments, the insertion handle 1022 may be omitted. In such a case, a different tape length may be selected such that the stop 1036 engages a portion or end of the nail 1024.

Figure 26:
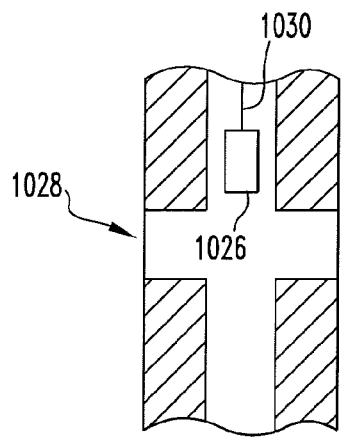
FIG. 26 is a partial cross-sectional view of the intramedullary nail shown in FIG. 25.

FIG. 26 illustrates a detailed view of the intramedullary nail 1024, the sensor 1026, and the hole 1028. The sensor 1026 may be aligned with the hole 1028, adjacent the hole 1028, or offset from the hole 1028. In the depicted embodiment, the sensor 1026 is generally adjacent to the hole 1028.

In use, the intramedullary nail 1024 is placed into the bone 100. The insertion handle 1022 may be attached to the intramedullary nail 1024. The probe 1029 is fed through the cannulation of the insertion handle 1022 and into the cannulation of the intramedullary nail 1024 until the stop 1036 engages the insertion handle 1022. In one particular embodiment, the wire 1030 is coupled to the control unit 1012, and the sensors 1026, 1020, and 1032 are calibrated using the control unit 1012. In some embodiments, the probe 1029 may be removed after calibration. If so, the third sensor 1032 and a transformation matrix may be used to identify the relative position of the second sensor 1020 and hence landmark identifier 1016. Optionally, the user may use transfixion elements, such as screws, to first lock the proximal end of the intramedullary nail. An operator uses the landmark identifier 1016 and the first sensor 1026 to identify the landmarks 1028. For example, in the case of intramedullary nail fixation, a surgeon uses the landmark identifier 1016 to identify the blind transfixion holes and drill through the holes for placement of a transfixion element.

Figure 27:
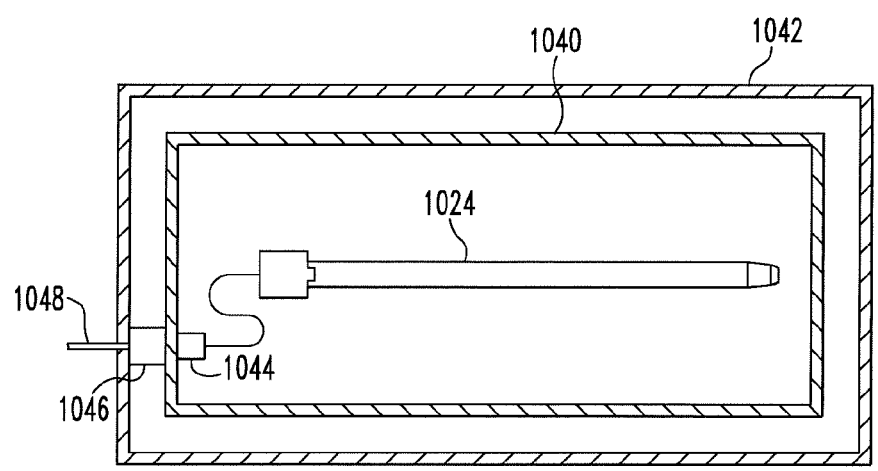
FIG. 27 illustrates a disclosed packaging for the intramedullary nail shown in FIGS. 25-26.

FIG. 27 illustrates a packaging embodiment. In general, intramedullary nails must be sterilized before implantation. If the sensor is installed in the intramedullary nail prior to serialization, the sensor may lose its calibration during the serialization process, particularly if the sterilization process involves radiation. For example, gamma radiation may be used to sterilize hermetically sealed components, such as the sensor. The embodiment depicted in FIG. 27 illustrates a way to maintain the sterilization of the intramedullary nail while allowing for recalibration of the sensor. The embodiment depicted in FIG. 27 may include a first package 1040, a second package 1042, a first connector 1044, a second connector 1046, and a cable 1048. In the depicted embodiment, a sensor (not shown) and intramedullary nail 1024 are located within the first package 1040. Alternatively, the probe 1029 and the sensor are located within the first package 1040. In yet another example, only the sensor is located within the first package 1040. A memory device (not shown) may be coupled to the sensor. The memory device may be used to store a calibration transformation matrix (x1, y1, z1, x2, y2, z2) as well as other data, such as length and size of the intramedullary nail or the probe. The memory device may be mounted to or placed on the intramedullary nail 1024 or the probe 1029. The first connector 1044 is electrically connected, but removably attached, to the second connector 1046. The first connector 1044 is also electrically coupled to the sensor or the memory device. The first package 1040 maintains the sterilization of the device held within. The cable 1048 is electrically coupled to the second connector 1046 and a storage device (not shown). The calibration for the sensor is downloaded from the storage device and transmitted through the connectors 1044, 1046 to the sensor or the memory device. The calibration step may be performed during manufacturing of the system or immediately prior to implantation of the implant.

Figure 28:
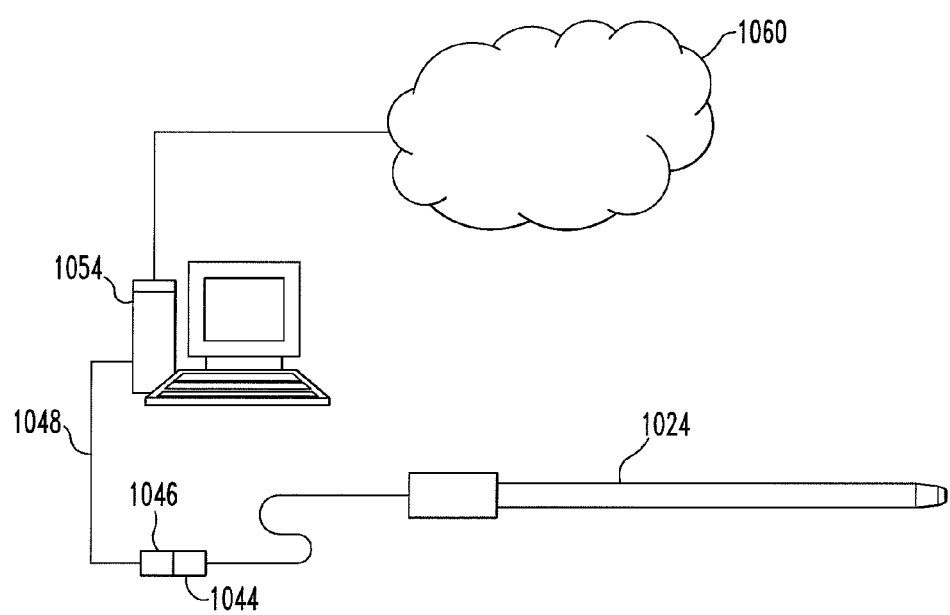
FIG. 28 illustrates a disclosed method for connecting a disclosed system to a network.

FIG. 28 illustrates a method of connecting the system 1010 to a network. FIG. 28 illustrates a network 1060, a computing device 1050, the cable 1048, the second connector 1046, the first connector 1044, and the intramedullary nail 1024. In the depicted embodiment, a sensor (not shown) is located within the intramedullary nail 1024. Alternatively, the sensor may be attached to the probe 1029 or freestanding. In some embodiments, the intramedullary nail 1024 may be wrapped in packaging, such as the first package 1040 and/or second package 1042 but this is not always the case. A memory device (not shown) may be coupled to the sensor. The memory device may be used to store a calibration transformation matrix (x1, y1, z1, x2, y2, z2) as well as other data, such as length and size of the intramedullary nail or the probe. The memory device may be mounted to or placed on the intramedullary nail 1024 or the probe 1029. The network 1060 maybe a local area network or a wide area network. The computing device 1054 is coupled to the network 1060. In some embodiments, the network communication may be encrypted. The cable 1048 connects the computing device 1054 to the sensor or the memory device through the use the connectors 1044, 1046. In this way, the sensor calibration may be downloaded from the computing device 1054 and/or the network 1060. While the depicted embodiment illustrates the sensor within the intramedullary nail, this is not always the case. The sensor may be attached to the probe or freestanding. In some embodiments, the memory device may be located within the control unit, and the control unit is coupled to the network to download the calibration data.

Figure 29:
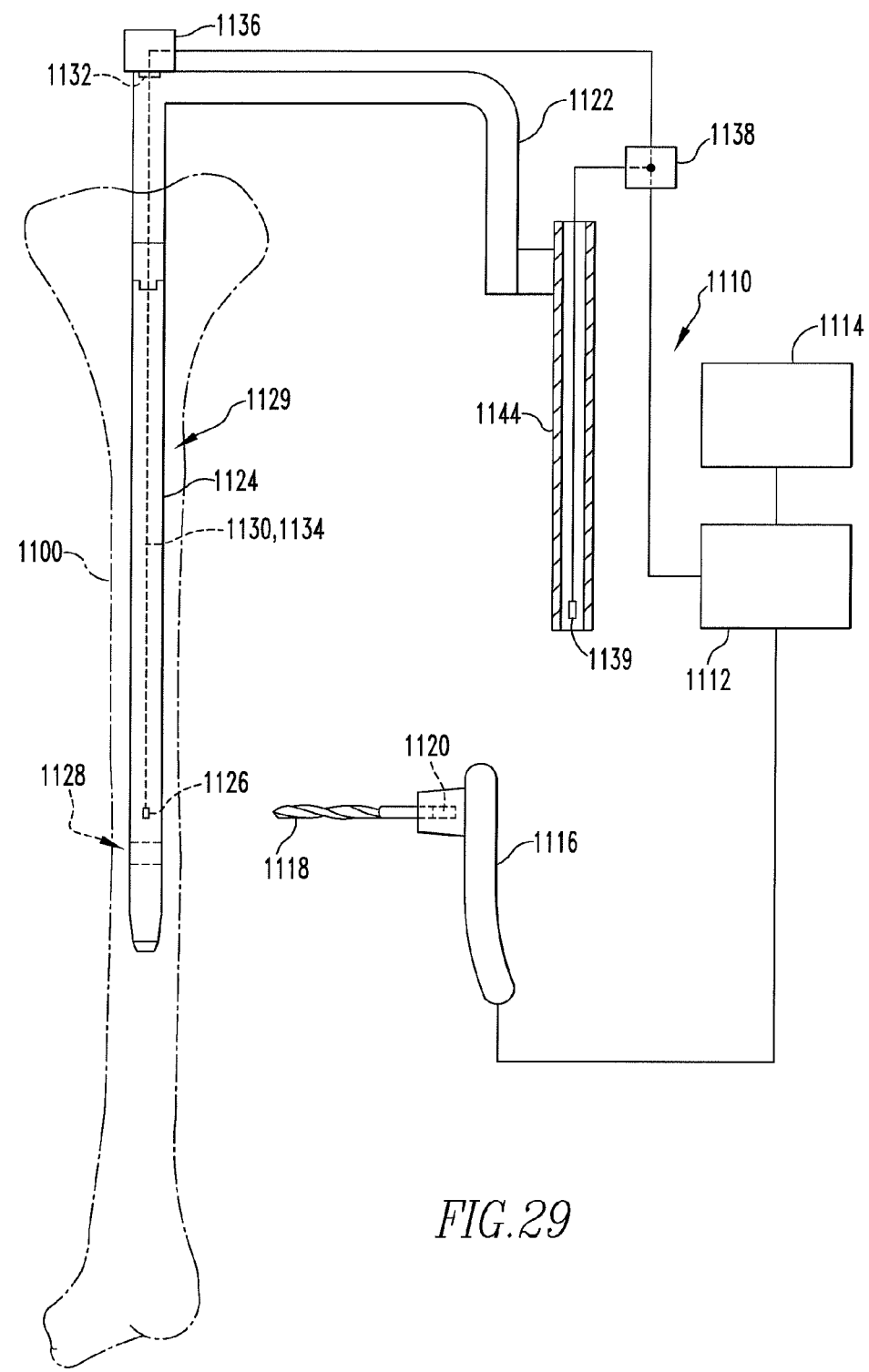
FIG. 29 illustrates yet another disclosed system for identifying a landmark.

FIG. 29 illustrates another system 1110 for identifying landmarks. The system 1110 may include a control unit 1112, a field generator 1114, a landmark identifier 1116, an intramedullary nail 1124, a drop 1136, and a probe 1129. The control unit 1112 may be included as part of the processor described above or may be a separate unit. The intramedullary nail 1124 is inserted into the bone 100, and the intramedullary nail 1124 has a hole or landmark 1128. In the depicted embodiment, the field generator 1114 is coupled to the control unit 1112, either by wire or wirelessly. In the depicted embodiment, an insertion handle 1122 is removably attached to the intramedullary nail 1124. The insertion handle 1122 and/or the intramedullary nail 1124 may be cannulated. In some embodiments, the insertion handle 1122 may include a third sensor 1144. The drop 1136 may include a fourth sensor 1139.

The landmark identifier 1116 may include a second sensor 1120. The landmark identifier 1116 may guide a drill bit 1018, and the drill bit 1018 may be coupled to a drill (not shown). The second sensor 1120 may be coupled to the control unit 1112, either by wire or wirelessly. In some embodiments, the field generator 1114 may be directly mounted on the landmark identifier 1116.

The probe 1129 may include a wire 1130, a tape 1134, and a stop 1136. The tape 1134 may have, in some embodiments, a rectangular geometry that assists in orienting the tape as it is placed into a cannulation of the intramedullary nail 1124. In some embodiments, the wire 1130 may be operatively coupled to the tape 1134. For example, this may be accomplished through the use of an adhesive or fastener. A first sensor 1126 is coupled to the control unit 1112, either by wire or wirelessly. In the depicted embodiment, the first sensor 1126 is connected through the use of the wire 1130. In some embodiments, a detachable connector may be used. The first sensor 1126 may be coupled to a distal end of the tape 1134, and the stop 1136 may be coupled to a proximal end of the tape 1134. The stop 1136 may be used to control the placement of the sensor 1126. If the tape 1134 is a fixed length and the distance is known from the end of the insertion handle to the landmark 1128, repeatable placement of the first sensor 1126 may be achieved. The tape 1134 may be of sufficient length such that the sensor 1126 is aligned with the landmark 1128, adjacent the landmark 1128, or offset from the landmark 1128.

In use, the intramedullary nail 1124 is placed into the bone 100. The insertion handle 1122 may be attached to the intramedullary nail 1124. The probe 1129 is fed through the insertion handle 1122 and into the intramedullary nail 1124 until the stop 1136 engages the insertion handle 1122. In one particular embodiment, the wire 1130 is coupled to the control unit 1112, and the sensors 1126, 1120, and 1132 are calibrated using the control unit 1112. In some embodiments, the probe 1129 may be removed after calibration. If so, the third sensor 1132 and/or the fourth sensor 1139 and a transformation matrix may be used to identify the relative position of the second sensor 1120 and hence targeter 1116. Optionally, the user may use transfixion elements, such as screws, to first lock the proximal end of the intramedullary nail. An operator uses the landmark identifier 1116 and the first sensor 1126 to identify the landmarks 1128. For example, in the case of intramedullary nail fixation, a surgeon uses the landmark identifier 1116 to identify the blind transfixion holes and drill through the holes for placement of a transfixion element.

Figure 30:
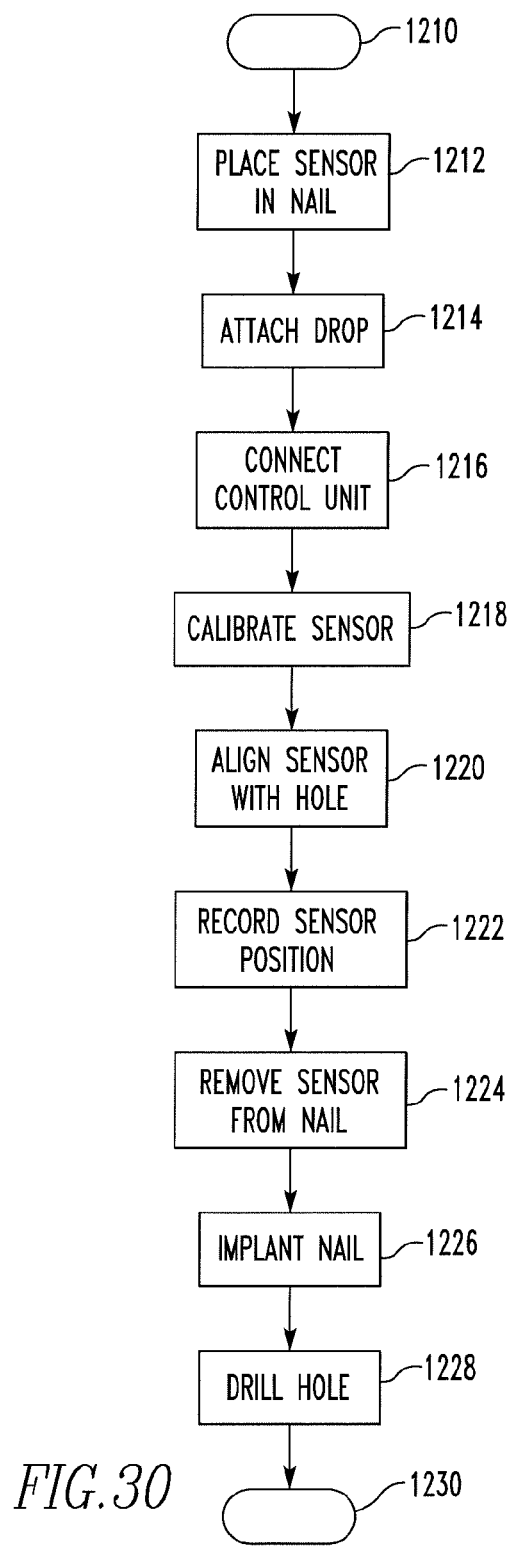
FIG. 30 is a flowchart illustrating a disclosed method of using the disclosed systems for identifying landmarks.

FIG. 30 illustrates one disclosed method for using the system to identify a landmark. The method begins at step 1210. In step 1212, the sensor is placed in the nail. In step 1214, the insertion handle is coupled to the nail, and the drop is attached to the insertion handle. In step 1216, the control unit is coupled to the sensor. In step 1218, the sensor is calibrated. In step 1220, the sensor is aligned with the hole. In step 1222 the sensor position is recorded through the use of the control unit. In step 1224, the sensor is removed from the nail. In step 1226, the nail is implanted into the bone. In step 1228, the hole is drilled using the targeter. The method stops in step 1230.

Figure 31:
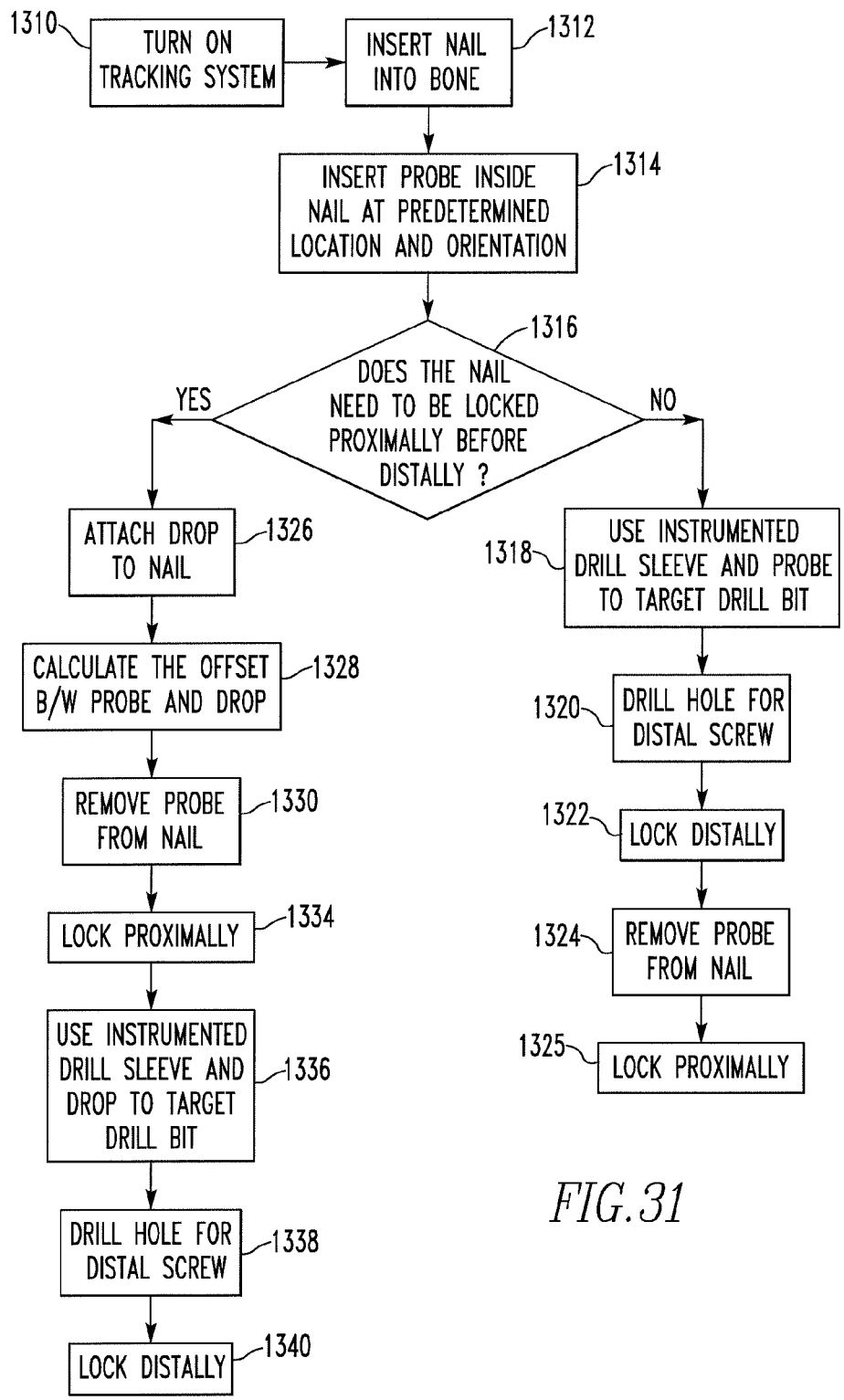
FIG. 31 is another flowchart illustrating another disclosed method for using the disclosed systems for identifying landmarks.

FIG. 31 illustrates another disclosed method for using the system to identify a landmark. In step 1310, the tracking system is turned on. In step 1312, the intramedullary nail is inserted into bone. In step 1314, the probe is inserted into the intramedullary nail canal at a predetermined location and orientation. In step 1316, there is a decision whether the intramedullary nail needs to be locked proximally before distally. If yes, then in step 1326 the drop is attached to the nail. In step 1328, an offset is calculated between the probe and the drop. In other words, a transformation matrix is created. Alternatively, the drop is not coupled to the intramedullary but instead a sensor mounted in the insertion handle is used to calculate an offset. In step 1330, the probe is removed from the nail. In step 1334, the nail is locked proximally. This may be accomplished through the use of the landmark identifier, a mechanical jig, or by manual operation. In step 1336, the landmark identifier is used to target the drill. In step 1338, the hole is drilled for the distal screw. In step 1340, the intramedullary nail is locked distally. On the other hand, if the decision is to lock distally first, then in step 1318 the landmark identifier and probe are used to target the drill bit. In step 1320, the hole is drilled for the distal screw. In step 1322, the intramedullary nail is locked distally. In step 1324, the probe is removed from the intramedullary nail. In step 1324, the intramedullary nail is locked proximally. This may be accomplished through the use of the landmark identifier, a mechanical jig, or by manual operation.

FIG. 32 illustrates a system for measuring depth of drill bit placement. The system 1400 may include a stator 1410 and a slider 1412. The stator 1410 and the slider 1412 form a capacitive array that can sense relative motion. Moving the stator 1410 and the slider 1412 in a linear relation relative to one another causes a voltage fluctuation that can be interpreted and used to determine the distance traveled. In some embodiments, an electronic measuring circuit (not shown) and the slider 1412 may be housed inside the landmark identifier, and the drill bit may be specially constructed to have the stator 1410 along outer surface so that the stator 1410 and the slider 1412 are in very close linear proximity to each other. The linear movement of the drill bit stator 1410 induces a voltage in the receiving slider 1412 which is interpreted by the electronic measuring circuit as a distance measurement. The distance measurement may be sent to the control unit and/or displayed on the monitor. Capacitive sensors are highly susceptible to moisture, and so some embodiments may be made to prevent liquids, such as bodily fluids, from traveling between the stator 1410 and the slider 1412. O-rings or some other similar form of wipes can be incorporated within the landmark identifier in order to keep the drill bit substantially moisture free.

Figure 33A:
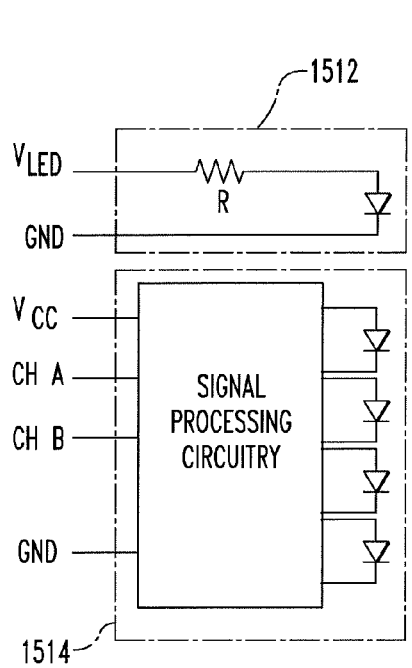
FIGS. 33A and 33B illustrate another disclosed device for tracking drill depth.
Figure 33B:
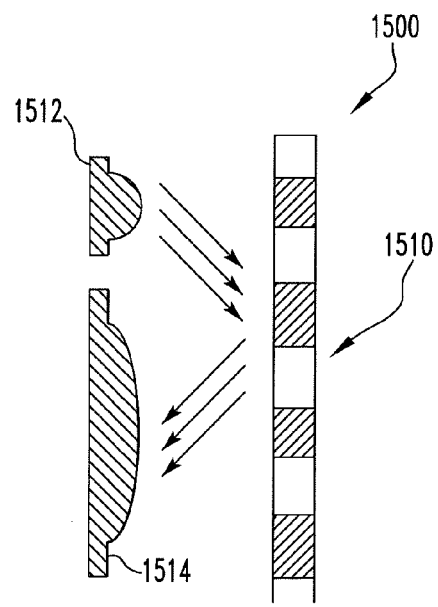
Figure 34:
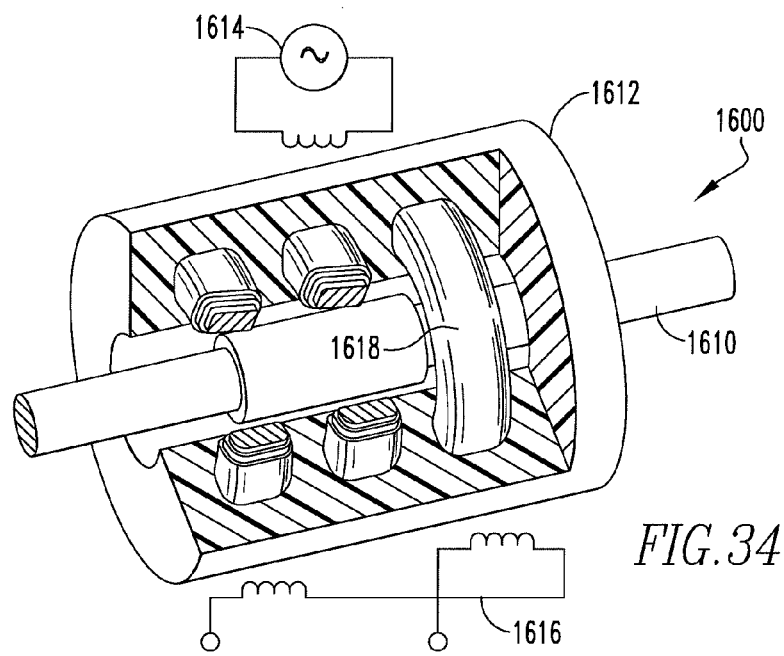
FIG. 34 illustrates yet another disclosed device for tracking drill depth.

FIGS. 33A and 33B illustrate another system for measuring depth of drill bit placement. The system 1500 may include a reflective code wheel or strip 1510, a lens 1512, and an encoder 1514. The lens 1512 focuses light onto bar of the code strip 1510. As the code strip 1510 rotates, an alternating pattern of light and shadow cast by the window and bar, respectively, falls upon photodiodes of the encoder 1514. The encoder 1514 converts this pattern into digital outputs representing the code strip linear motion. In the depicted embodiment, the encoder is an Avago Technologies AEDR-8300 Reflective Optical Encoder available from Avago Technologies of 350 W Trimble Road, San Jose, Calif. Alternatively, the Avago Technologies ADNS-5000 One Chip USB LED-based Navigation System may be used. The encoder and its supporting electronics may be mounted inside the landmark identifier so that its input region is oriented toward a "window" in the landmark identifier cannulation. Markings, such as dark colored concentric rings or bright reflective rings, may be added to the drill bit in order to enhance the visibility of the bit to the encoder. These markings could also be used to denote the starting zero point for measurement. As the drill bit moves linearly within the landmark identifier, the encoder measures the movement of the drill bit. The distance measurement may be sent to the control unit and/or displayed on the monitor.

FIG. 34 illustrates yet another system for drill depth measurement. The system 1600 utilizes a Linear Variable Differential Transformer (LED) 1612. An LVDT is a type of electrical transformer used to measure linear displacement. The LVDT 1612 may include a plurality of solenoidal coils 1618 placed end-to-end around a tube 1610, which is the landmark identifier in the depicted embodiment. In the embodiment depicted in FIG. 34, the center coil is the primary coil and the outer two coils are the secondary coils. A cylindrical ferromagnetic core 1610, such as the drill bit, slides along the axis of the tube. An alternating current 1614 is driven through the primary coil, causing a voltage to be induced in each secondary proportional to its mutual inductance with the primary. A pickup sensor 1616 measures the magnitude of the output voltage, which is proportional to the distance moved by the core (up to its limit of travel). The phase of the voltage indicates the direction of the displacement. Because the sliding core does not touch the inside of the tube, it can move without friction, making the LVDT a highly reliable device. The absence of any sliding or rotating contacts allows the LVDT to be completely sealed against the environment. The distance measurement may be sent to the control unit and/or displayed on the monitor.

Figure 35:
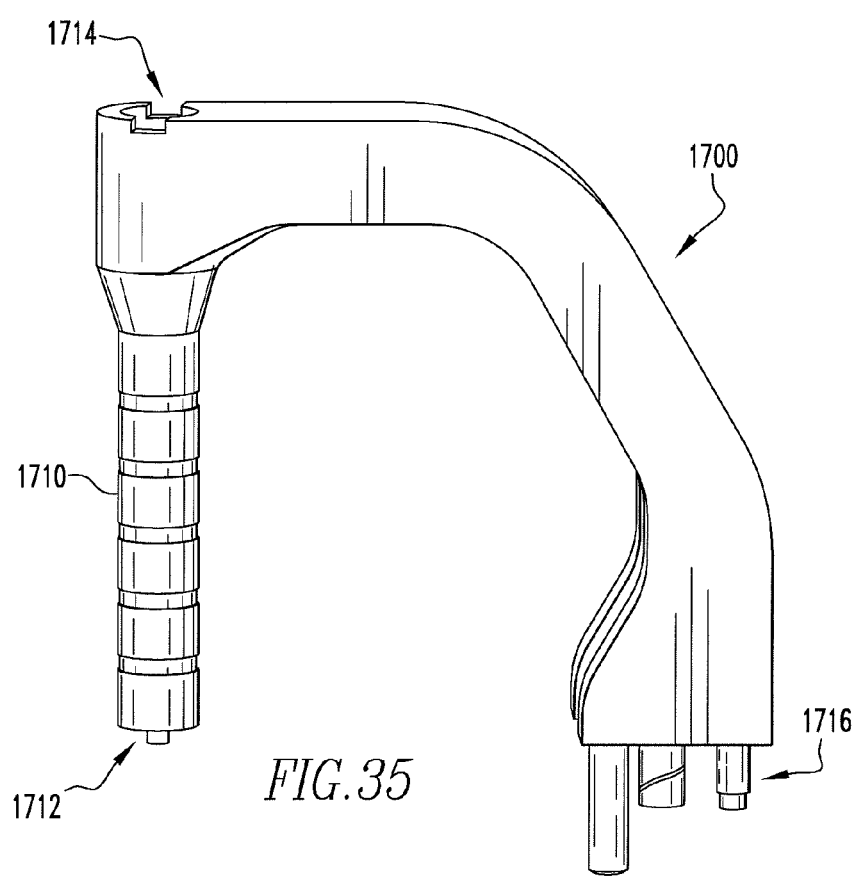
FIG. 35 illustrates another disclosed insertion handle.
Figure 36:
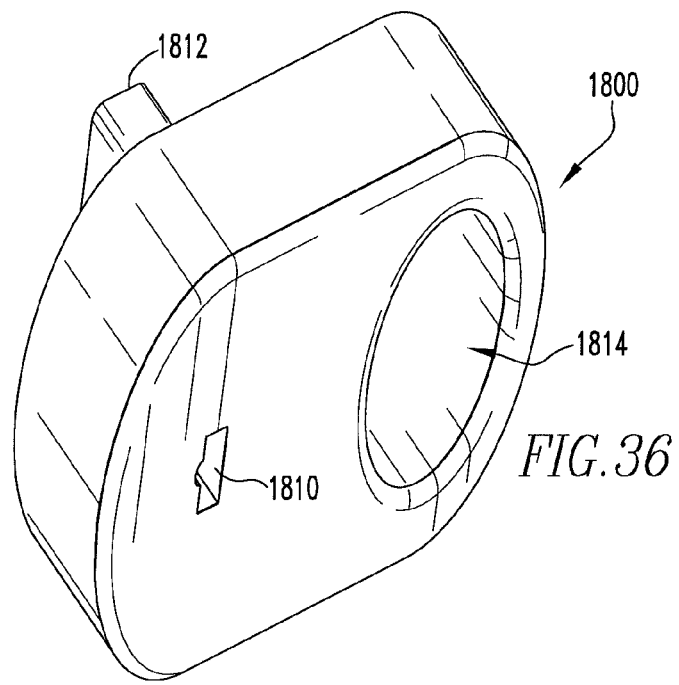
FIG. 36 is a top perspective view of an adjustable stop.
Figure 37:
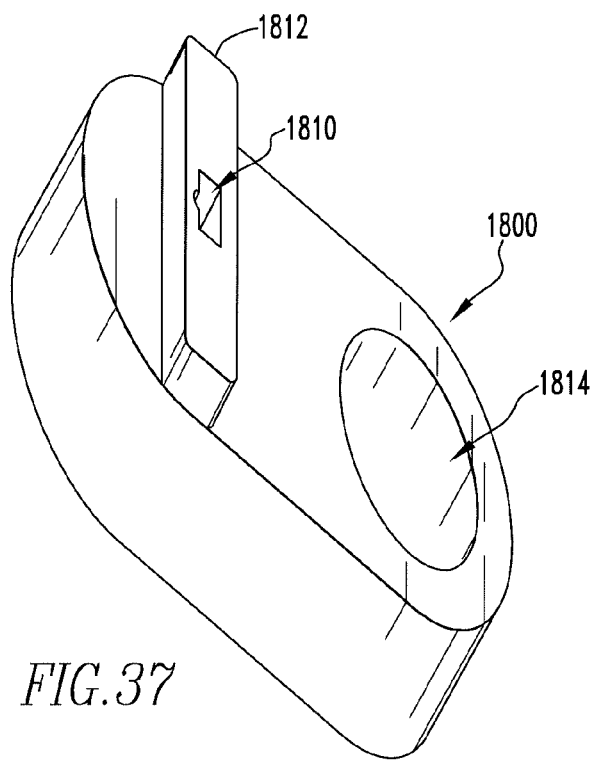
FIG. 37 is a bottom perspective view of the adjustable stop shown in FIG. 36.

FIGS. 35-37 illustrate an insertion handle 1700 and an adjustable stop 1800. The insertion handle 1700 a stem 1710 that connects to an implant, such as an intramedullary nail (not shown), at an end portion 1712. The insertion handle 1700 may include a quick connect 1716 for attachment to a drop, proximal targeting device, or some other instrument or apparatus. The insertion handle may include a top portion 1714, which may include a hole and/or an alignment feature. The adjustable stop 1800 may include a slot 1810, an alignment member 1812, and a fastener hole 1814.

In the embodiments depicted in FIGS. 35-37, the adjustable stop 1800 may be removably attached to the top portion 1714. In some embodiments, the adjustable stop may be integrally formed with the insertion handle 1700. In yet other embodiments, the adjustable stop may be permanently attached to the insertion handle 1700. In the depicted embodiment, the alignment member 1812 fits within an alignment feature of the top portion to prevent rotation of the adjustable stop. A fastener (not shown) may be placed through the fastener hole 1814 to attach the adjustable stop to the insertion handle 1700. The tape 1034, 1134 may be placed through the slot 1810, through the stem 1710, and into the intramedullary nail cannulation. The slot 1810 may have a shape to match the geometry of the tape to aid in its insertion or to prevent rotation of the tape. The tape 1034, 1134 may include markings, graduations, or detents to indicate an appropriate depth for the given nail length. In some embodiments, the adjustable stop 1800 may include a locking mechanism (not shown) to temporarily lock the tape 1034, 1134 at a particular depth. In its simplest form, the locking mechanism may be a fastener that frictionally engages the tape 1034, 1134.

Figure 38:
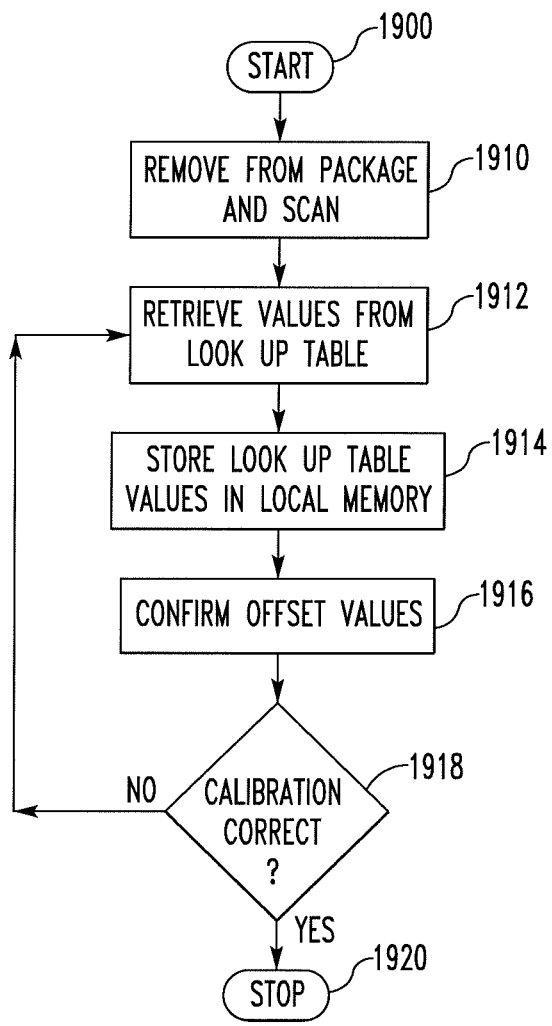
FIG. 38 is a flowchart that illustrates a disclosed method of calibrating the disclosed systems for locating landmarks.

FIG. 38 illustrates a method for calibrating the system for identifying landmarks. Calibration is necessary for accuracy. The method begins at step 1900, which may include powering up the system. In step 1910, the probe and the landmark identifier are removed from packaging, if any, and scanned. In some embodiments, the drop is also scanned. Scanning may include reading a bar code using a bar code reader. Scanning causes the system to retrieve offset sensor values that correspond to the bar code from a look up table in step 1912. The look up table may be local or accessed over a network, such as the Internet. Alternatively, the probe and the landmark identifier may include a serial number or other unique identifier, and the unique identifier is used in conjunction with the look up table to retrieve offset sensor values. The offset sensor values are stored in local memory of the system in step 1914. In step 1916, the user places the probe relative to the implant and attempts to track a landmark using the landmark identifier in step 1916. In step 1918, there is a decision whether the calibration is correct. If so, the method ends in step 1920. Otherwise, new offset values are retrieved in step 1912.

In one particular embodiment, provided feedback information is selected from the group consisting of audible, visual, and tactile. The audible feedback may be output through a speaker, headphones, ear buds, or an ear piece. The audible feedback signal may be transmitted over wire or wirelessly using radio frequency or terrestrial data transmission. The visual feedback may be output through a cathode ray tube, a liquid crystal display, or a plasma display. Visual feedback devices may include, as examples, a television monitor, a personal digital assistant, or a personal media player. The visual feedback signal may be transmitted over wire or wirelessly using radio frequency or terrestrial data transmission. The tactile feedback may be output through gloves, instruments, or a floor mat. The tactile feedback signal may be transmitted over wire or wirelessly using radio frequency or terrestrial data transmission.

Methods for identifying landmarks are also disclosed. One disclosed method may include the steps of: providing an orthopedic implant assembly having an orthopedic implant with a longitudinal groove and a removable lead having a magnetic sensor attached thereto situated within the longitudinal groove, the orthopedic implant having a proximal end portion, a distal end portion, and at least one landmark on the distal end portion; implanting the orthopedic implant assembly in a patient; first installing transfixion elements in the proximal end portion; identifying the at least one landmark using a landmark identifier; installing a transfixion element in the at least one landmark in the distal end portion after first installing transfixion elements in the proximal end portion; and removing the removable lead. This method allows for proximal locking of the implant prior to distal locking. This is a significant advantage over the prior art as prior devices required distal locking prior to proximal locking.

System calibration may be accomplished during manufacturing, after distribution, or immediately preceding implant implantation. The calibration step is analogous to registration in computer assisted surgery. Calibration may be needed for different reasons. For example, sensor calibration may be needed to correct for manufacturing tolerances. The system may be designed based upon a computer-aided-design model, and calibration is used to accurately place the sensors relative to one another. The processor or the control unit may include software to generate X, Y, Z, pitch, yaw, and roll offset values to locate the sensors in a global coordinate system or simply placement relative to one another. In one embodiment, the system is manufactured and calibrated during manufacturing and assigned a unique identifier, such as a serial number, color code, bar code, or RFID tag. If the system needs to be re-calibrated, the unique identifier may be used to retrieve the offset values, either locally or over a network. Further, the unique identifier may be used to retrieve other data, such as the size of the intramedullary nail or the length of the intramedullary nail and/or the probe.

Thus, various systems (10, 110, 1010, 1110) for identifying landmarks are disclosed. The disclosed systems may include a field generator (16, 116, 1016, 1116) for generating a magnetic field, an orthopedic implant (30, 130, 1030, 1130) located within the magnetic field, the implant having at least one landmark (31, 131, 1028, 1128), an optional removable probe (1029, 1129), a first magnetic sensor (32, 132, 1026, 1126), a landmark identifier (18, 118, 1016, 1116) with an optional second magnetic sensor (20, 120, 1020, 1120) and a processor (12, 112, 1012, 1112) for comparing sensor data from the first and second sensor or from the first sensor and landmark identifier and using the set distance to calculate the position of the landmark identifier (18, 118, 1016, 1116) relative to the at least one landmark (31, 131, 1028, 1128). The systems (10, 110, 1010, 1110) allow for blind targeting of one or more landmarks (31, 131, 1028, 1128).

As various modifications may be made in the constructions and methods herein described and illustrated without departing from the scope of this disclosure, it is intended that all matter contained in the foregoing description or shown in the accompanying drawings shall be interpreted as illustrative rather than limiting. For example, while FIG. 1 illustrates a pocket for affixing the first sensor to the implant, other structure and/or methods may be used to affix these items together. Thus, the breadth and scope of this disclosure should not be limited by any of the above-described exemplary embodiments, but should be defined only in accordance with the following claims appended hereto and their equivalents.

The invention claimed is:

1. A system for identifying a landmark, the system comprising:
    a field generator for generating a magnetic field;
    an orthopedic implant having at least one landmark, the orthopedic implant defining a cannulation and a longitudinal groove, the longitudinal groove having a proximal end region and a distal end region, wherein the orthopedic implant defines a first opening in an exterior surface of the orthopedic implant, the first opening being open to the longitudinal groove, and wherein, at a location adjacent the opening, the orthopedic implant defines a second opening to receive a cover for the first opening;
    a cover that is insertable into the second opening such that the cover covers the first opening and is substantially flush with an external surface of the implant when disposed in the second opening;
    a first magnetic sensor mounted to the orthopedic implant, the first magnetic sensor comprising one or more sensor coils disposed in a sensor housing, the first magnetic sensor being located in the distal end region of the longitudinal groove and being spaced apart from the at least one landmark a set distance, the first magnetic sensor being configured to produce sensor data responsive to the magnetic field;
    a landmark identifier; and
    a processor configured to analyze sensor data from the first magnetic sensor and data from the landmark identifier and use the set distance to calculate a position of the landmark identifier relative to the at least one landmark.

2. The system of claim 1, wherein the landmark is selected from the group consisting of a structure, a void, a boss, a channel, a detent, a flange, a groove, a member, a partition, a step, an aperture, a bore, a cavity, a dimple, a duct, a gap, a notch, an orifice, a passage, a slit, a hole, or a slot.

3. The system of claim 1, wherein the orthopedic implant is an intramedullary nail.

4. The system of claim 1, wherein the orthopedic implant has an outer surface, an inner surface defining the cannulation, and a wall therebetween, and the first magnetic sensor is mounted within the wall.

5. The system of claim 1, wherein the orthopedic implant further comprises a pocket and the first magnetic sensor is located within the pocket.

6. The system of claim 1, further comprising an insertion handle removably coupled to the orthopedic implant.

7. The system of claim 1, further comprising a monitor electrically coupled to the processor.

8. The system of claim 1, wherein the longitudinal groove is disposed along an outer surface of the implant.

9. The system of claim 1, wherein the longitudinal groove is generally adjacent the cannulation.

10. The system of claim 9, further comprising a removable lead coupled to the first magnetic sensor.

11. The system of claim 1, wherein the landmark identifier comprises a drill sleeve.

12. The system of claim 1, wherein the landmark identifier further comprises a serrated tip.

13. The system of claim 1, wherein the processor provides feedback information to a user.

14. The system of claim 1, wherein the field generator and landmark identifier are disposed within a common handheld housing.

15. The system of claim 1, wherein the orthopedic implant has an inner surface that defines the cannulation, and the longitudinal groove is defined in the inner surface.

16. The system of claim 1, wherein at least one end of the cannulation ends at an opening defined in an exterior surface of the orthopaedic implant.

17. The system of claim 1, wherein the longitudinal groove is offset from the cannulation such that the magnetic sensor is located at least partially outside the cannulation.

18. The system of claim 1, wherein the longitudinal groove extends from the distal end region of the orthopaedic implant to a proximal end of the orthopaedic implant.

19. A system for identifying a landmark, the system comprising:
    a field generator for generating a magnetic field;
    an orthopedic implant located within the magnetic field, the orthopedic implant having at least one landmark, the orthopedic implant defining an internal cannulation and a longitudinal groove that extends generally adjacent the cannulation, the longitudinal groove having a proximal end region and a distal end region, the longitudinal groove being defined in a wall of the orthopedic implant between an outer surface of the wall and an inner surface of the wall that defines the cannulation, wherein the longitudinal groove has a diameter and is located in the wall of the orthopedic implant such that the diameter is contained between the outer surface and the inner surface;

an insertion handle removably attached to the orthopedic implant;

a first magnetic sensor placed within the orthopedic implant at the distal end portion of the longitudinal groove and spaced apart from the at least one landmark a set distance;

a landmark identifier; and a processor for comparing sensor data from the first sensor and landmark identifier using the set distance to calculate the position of the landmark identifier relative to the at least one landmark, wherein communication or power leads are routed to the first magnetic sensor through the insertion handle.

20. The system of claim 19, wherein the field generator and landmark identifier are disposed within a common handheld housing.

21. The system of claim 19, wherein communication and power leads are routed to the first magnetic sensor through the insertion handle.

22. A system for identifying a landmark, the system comprising:

a field generator for producing a set of multiple different magnetic field distributions;

an orthopedic implant having at least one landmark, the orthopedic implant defining an internal cannulation and a longitudinal groove that extends generally adjacent the cannulation, the longitudinal groove having a proximal end region and a distal end region, the longitudinal groove being defined in a wall of the orthopedic implant between an outer surface of the wall and an inner surface of the wall that defines the cannulation, the longitudinal groove being closed to the cannulation wherein the longitudinal groove has a diameter and is located in the wall of the orthopedic implant such that the diameter is contained between the outer surface and the inner surface;

a first magnetic sensor mounted to the orthopedic implant, the first magnetic sensor being located in the distal end region of the longitudinal groove and being spaced apart from the at least one landmark a set distance, the first magnetic sensor being configured to produce sensor data responsive to the magnetic field;

a removable lead coupled to the first magnetic sensor, the removable lead being disposed in the longitudinal groove and extending from a proximal end of the orthopaedic implant;

a landmark identifier; and a processor configured to analyze sensor data from the first magnetic sensor and data from the landmark identifier and use the set distance to calculate a position of the landmark identifier relative to the at least one landmark.

* * * * *